United States Patent
Duenas

(10) Patent No.: US 8,936,563 B2
(45) Date of Patent: Jan. 20, 2015

(54) METHOD FOR CONNECTING A BLOOD PUMP WITHOUT TRAPPING AIR BUBBLES

(75) Inventor: Benjamin Duenas, Mexico City (MX)

(73) Assignee: Vitalmex International S.A. de C.V., Mexico City (MX)

( * ) Notice: Subject to any disclaimer, the term of this patent is extended or adjusted under 35 U.S.C. 154(b) by 509 days.

(21) Appl. No.: 13/276,117

(22) Filed: Oct. 18, 2011

(65) Prior Publication Data

US 2012/0035412 A1    Feb. 9, 2012

Related U.S. Application Data

(62) Division of application No. 12/413,377, filed on Mar. 27, 2009, now Pat. No. 8,092,416.

(60) Provisional application No. 61/040,612, filed on Mar. 28, 2008.

(51) Int. Cl.
  *A61M 37/00* (2006.01)
  *A61M 1/00* (2006.01)
  *A61N 5/06* (2006.01)
  *A61M 5/36* (2006.01)
  *A61M 1/10* (2006.01)
  (Continued)

(52) U.S. Cl.
  CPC .............. *A61M 5/36* (2013.01); *A61M 1/1037* (2013.01); *A61M 39/02* (2013.01); *A61M 1/1008* (2013.01); *A61M 1/122* (2013.01)
  USPC .......... 604/6.16; 604/6.1; 604/6.14; 604/122; 606/16

(58) Field of Classification Search
  CPC ....................... A61M 1/3626; A61M 2039/205
  USPC ............... 604/6.16, 4.01, 6.1, 6.14, 122, 533; 606/16
  See application file for complete search history.

(56) References Cited

U.S. PATENT DOCUMENTS 4,123,091 A    10/1978    Cosentino et al.
4,627,419 A    12/1986    Hills
(Continued)

FOREIGN PATENT DOCUMENTS

CA    1225895    8/1987
DE    3637702 A1    5/1988
(Continued)

OTHER PUBLICATIONS

Sacristan E. Corona F., Rodriguez G., Duenas B., Gorzelewski A., Calderon M. "Development of a Universal Second Generation Pneumatic Ventricular Assist Deviceand Driver Unit", 25th Annual IEEE-EMBS Conference 2003, pp. 427-430 (4 pages).
(Continued)

*Primary Examiner* — Leslie Deak
(74) *Attorney, Agent, or Firm* — Ladas & Parry LLP

(57) ABSTRACT

A method for connecting medical tubing or any other type of fluidic circuit conduits (e.g., cannulae) to a ventricular assist device ("VAD") or any other pumping device used for blood pumping during cardiac circulatory support for vascular surgery. The method prevent air bubbles from entering a cardiac circulatory support system when connecting cannulae to a VAD that may later enter the blood stream of a patient during cardiac surgery, and also provide for purging any air bubbles that may have entered the cardiac circulatory support system during a cannulae-VAD connection.

10 Claims, 24 Drawing Sheets

(51) Int. Cl.
*A61M 39/02* (2006.01)
*A61M 1/12* (2006.01)

(56) References Cited

U.S. PATENT DOCUMENTS

| | | | |
|---|---|---|---|
| 4,662,355 A | 5/1987 | Pieronne et al. |
| 4,671,786 A | 6/1987 | Krug |
| 4,782,689 A | 11/1988 | DeRome |
| 4,811,737 A | 3/1989 | Rydell |
| 4,838,889 A | 6/1989 | Kolff |
| 4,888,980 A | 12/1989 | DeRome |
| 4,904,289 A | 2/1990 | Miyakami et al. |
| 4,929,243 A | 5/1990 | Koch et al. |
| 4,969,879 A | 11/1990 | Lichte |
| 4,990,311 A | 2/1991 | Hirai et al. |
| 5,015,442 A | 5/1991 | Hirai |
| 5,035,705 A | 7/1991 | Burns |
| 5,152,077 A | 10/1992 | Liang |
| 5,178,612 A | 1/1993 | Fenton, Jr. |
| 5,224,933 A | 7/1993 | Bromander |
| 5,230,220 A | 7/1993 | Kang et al. |
| 5,312,337 A | 5/1994 | Flaherty et al. |
| 5,334,153 A | 8/1994 | McIntyre et al. |
| 5,369,892 A | 12/1994 | Dhaemers |
| 5,387,225 A | 2/1995 | Euteneuer et al. |
| 5,405,320 A | 4/1995 | Twardowski et al. |
| 5,405,339 A | 4/1995 | Kohnen et al. |
| 5,439,448 A | 8/1995 | Leschinsky et al. |
| 5,441,482 A | 8/1995 | Clague et al. |
| 5,509,897 A | 4/1996 | Twardowski et al. |
| 5,676,526 A | 10/1997 | Kuwana et al. |
| 5,702,364 A | 12/1997 | Euteneuer et al. |
| 5,707,356 A | 1/1998 | Paul |
| 5,772,261 A | 6/1998 | Magram |
| 6,134,806 A | 10/2000 | Dhaemers |
| 6,142,980 A | 11/2000 | Schalk |
| 6,203,532 B1 | 3/2001 | Wright |
| 6,319,231 B1 | 11/2001 | Andrulitis |
| 6,391,272 B1 | 5/2002 | Schroeder |
| 6,648,860 B2 | 11/2003 | Staats et al. |
| 6,783,522 B2 | 8/2004 | Fischell |
| 6,802,806 B2 | 10/2004 | McCarthy et al. |
| 6,845,569 B1 | 1/2005 | Kim |
| 6,890,316 B2 | 5/2005 | Rawles |
| 6,949,065 B2 | 9/2005 | Sporer et al. |
| 6,994,687 B1 | 2/2006 | Shkolnik |
| 7,004,924 B1 | 2/2006 | Brugger et al. |
| 7,074,176 B2 | 7/2006 | Sacristan et al. |
| 7,217,236 B2 | 5/2007 | Calderon et al. |
| 7,326,186 B2 | 2/2008 | Trombley, III et al. |
| 7,387,624 B2 | 6/2008 | Nelson |
| 7,404,686 B2 | 7/2008 | Volum |
| 7,479,102 B2 | 1/2009 | Jarvik |
| 7,544,160 B2 | 6/2009 | Gross |
| 7,588,530 B2 | 9/2009 | Heilman |
| 2002/0139124 A1 | 10/2002 | Palermo |
| 2002/0161322 A1 | 10/2002 | Utterberg |
| 2003/0088208 A1 | 5/2003 | Murphy et al. |
| 2004/0003511 A1 | 1/2004 | Silver |
| 2004/0146437 A1 | 7/2004 | Arts et al. |
| 2004/0161371 A1 | 8/2004 | Russell et al. |
| 2005/0010077 A1 | 1/2005 | Calderon |
| 2005/0089458 A1 | 4/2005 | Oke |
| 2006/0063964 A1 | 3/2006 | Massen |
| 2006/0074271 A1 | 4/2006 | Cottor |
| 2006/0104858 A1 | 5/2006 | Potember et al. |
| 2006/0129023 A1 | 6/2006 | Weatherbee |
| 2006/0142633 A1 | 6/2006 | Lane |
| 2006/0161040 A1 | 7/2006 | McCarthy |
| 2006/0178550 A1 | 8/2006 | Jenson |
| 2006/0217667 A1 | 9/2006 | Accisano |
| 2006/0229564 A1 | 10/2006 | Andersen |
| 2006/0229590 A1 | 10/2006 | Roy |
| 2006/0271016 A1 | 11/2006 | Fangrow |
| 2006/0284422 A1 | 12/2006 | Lunder |
| 2007/0001458 A1 | 1/2007 | Kertesz |
| 2007/0057509 A1 | 3/2007 | Beal |
| 2007/0060786 A1 | 3/2007 | Gura |
| 2007/0066862 A1 | 3/2007 | Vaska |
| 2007/0080536 A1 | 4/2007 | Park |
| 2007/0088324 A1 | 4/2007 | Fangrow |
| 2007/0088325 A1 | 4/2007 | Fangrow |
| 2008/0118395 A1 | 5/2008 | Benedek |

FOREIGN PATENT DOCUMENTS

| | | |
|---|---|---|
| DE | 19619261 C1 | 4/1997 |
| EP | 0248979 | 2/1987 |
| EP | 0269941 A1 | 6/1988 |
| EP | 1525892 | 4/2005 |
| EP | 2005-226861 A | 8/2005 |
| EP | 1629855 | 1/2006 |
| GB | 1243576 | 10/1972 |
| JP | 2071763 | 3/1990 |
| JP | 2121648 | 5/1990 |
| JP | 6121831 | 5/1990 |
| JP | 4053565 | 2/1992 |
| JP | 4231932 | 8/1992 |
| JP | 7023956 | 2/1995 |
| JP | 7059778 | 3/1995 |
| JP | 2001161668 | 6/2001 |
| JP | 2002-263181 A | 9/2002 |
| JP | 2004229886 | 8/2004 |
| JP | 20066528910 | 12/2006 |
| MX | 0400801 | 6/2005 |
| WO | 90/02572 A1 | 3/1990 |
| WO | WO 99/02209 | 1/1999 |
| WO | WO 03/001980 | 1/2003 |
| WO | 03/080375 A1 | 10/2003 |
| WO | WO 2005/023355 | 3/2005 |
| WO | WO 2006/019755 | 2/2006 |
| WO | 2008/103719 A1 | 8/2008 |
| WO | 2008/127315 A2 | 10/2008 |

OTHER PUBLICATIONS

Excobedo C., Tovar F., Suarez B., Hernandeza A., Corona F., Sacristan E., "Experimental and Computer-Based Performance Analysis of Tow Elastomer VAD Valve Designs", 27th Annual EEE-EMBS Conference 2005 (4 pages).

USPTO RR dated Jun. 7, 2011 in connection with U.S. Appl. No. 12/413,377.

USPTO Notice of Allowability mailed Aug. 20, 2011 in connection with U.S. Appl. No. 12/413,377.

USPTO RR dated May 5, 2014 in connection with U.S. Appl. No. 13/312,690.

USPTO NFOA dated Apr. 15, 2014 in connection with U.S. Appl. No. 13/276,148.

LVAD

RVAD

BI VAD

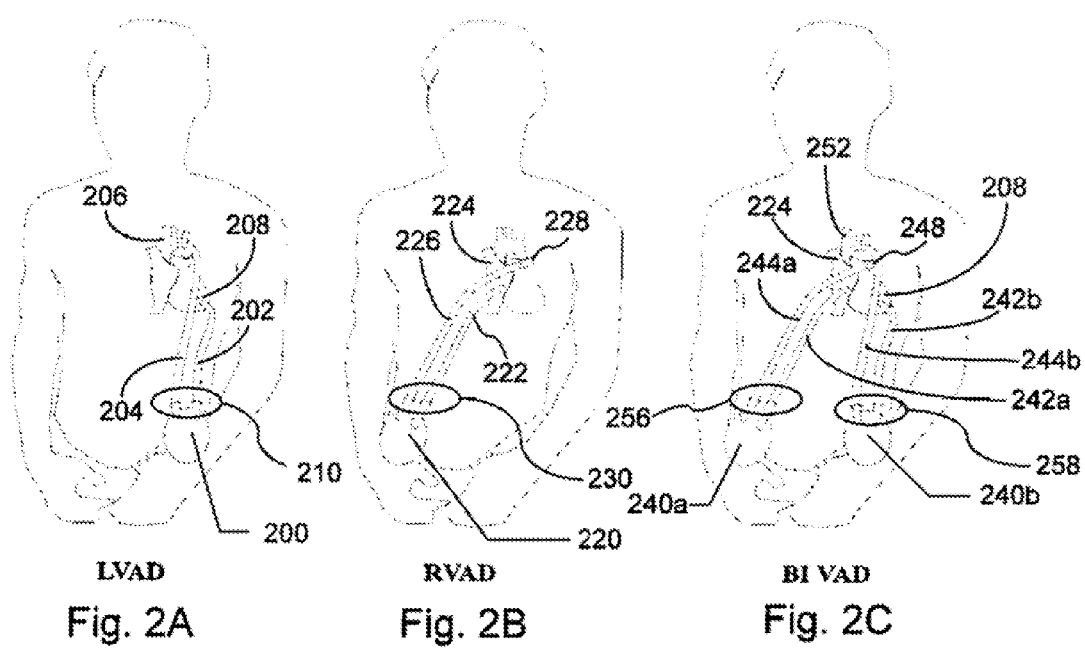

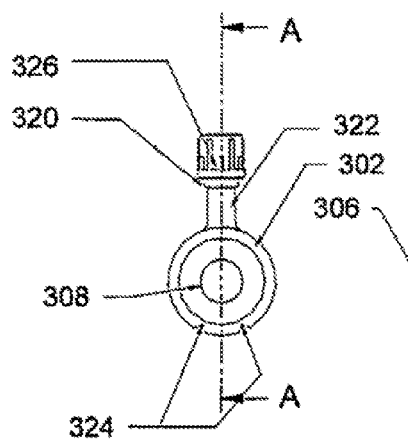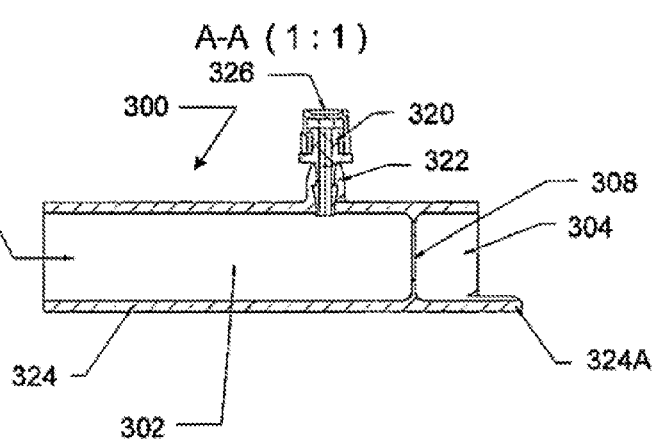
FIG. 5A                    FIG. 5B

METHOD FOR CONNECTING A BLOOD PUMP WITHOUT TRAPPING AIR BUBBLES

RELATED APPLICATION(S)

This application is a divisional application of U.S. Non-Provisional patent application Ser. No. 12/413,377 filed Mar. 27, 2009 for invention titled "Device and Method for Connecting a Blood Pump Without Trapping Air Bubbles", which claims priority under 35 U.S.C. §§119(e) to U.S. Provisional Patent Application No. 61/040,612 filed Mar. 28, 2008 for invention titled "Device and Method for Connecting a Blood Pump without Trapping Air Bubbles", both of which are incorporated by reference herein in their entireties.

BACKGROUND OF THE INVENTION

1. Field of the Invention

The present invention relates, in general, to interconnecting cannulae used with medical devices, and more particularly, to connecting and purging devices connected to cannulae for utilization in medical procedures.

2. Related Art

As heart disease has become more common in recent decades, for several reasons, which may include nutritional and life style choices, new and improved medical procedures have been developed to combat this medical condition. Procedures for treating or preventing heart failure typically require invasive surgery. Such procedures may involve using pumping devices for cardiac circulatory support before, during, and after the open heart surgery, or as a bridge in the case of a complete cardiopulmonary bypass, e.g., a heart transplant. Examples of cardiac circulatory support devices include rotary and axial blood pumps, as well as ventricular assist devices ("VADs"), which are used to supplement the heart's pumping action during and after surgery.

Cardiac circulatory support devices are connected to a patient's heart using medical tubing, (i.e., cannulae) that is connected to the heart at appropriate locations according to standard surgical practices. Some cardiac circulatory support systems include a pneumatic drive unit that connects to an air supply. The cardiac circulatory support systems may also include a pump that is magnetically or electrically powered.

FIGS. 1A-1C illustrate three examples of configurations of patient-implanted VADs. FIG. 1A shows a schematic illustration of a VAD 100 implanted in a patient as a left ventricular assist device, or LVAD. The LVAD 100 is connected to an outflow cannula 102, which is surgically connected to the left ventricle of the heart 108. The LVAD 100 is also connected to an inflow cannula 104, which is surgically connected to the patient's aorta 106. The LVAD 100 receives blood from the left ventricle 108 through the outflow cannula 102 and delivers the blood through the inflow cannula 104 to the aorta 106 for circulation throughout the patient's body.

FIG. 1B shows a schematic illustration of a VAD 120 implanted in a patient as a right ventricular assist device, or RVAD. The RVAD 120 is connected to an outflow cannula 122, which is surgically connected to the right atrium of the heart 124. The RVAD 120 is also connected to an inflow cannula 126, which is surgically connected to the pulmonary artery 128. The RVAD 120 receives blood from the right atrium 124 through the outflow cannula 122 and delivers the blood through the inflow cannula 126 to the pulmonary artery 128.

FIG. 1C shows a schematic illustration of two VADs 140a and 140b implanted in a patient as a bi-ventricular assist device, or RVAD. The BIVAD. The first VAD 140a is connected to an outflow cannula 142a, which is connected to the right atrium of the heart 124. The first RVAD 140a is also connected to an inflow cannula 144a, which is connected to the pulmonary artery 128. The second VAD is connected to an outflow cannula 142b, which is connected to the left ventricle of the heart 108. The second VAD 140b is also connected to an inflow cannula 144b, which is connected to the aorta 106. The BIVAD 140a, 140b assists the right atrium and the left ventricle, respectively of the heart 108 by combining the operations of both an RVAD and an LVAD.

FIGS. 2A-2C illustrate three examples of configurations of an extra-corporeal VAD. FIG. 2A shows a schematic illustration of a VAD 200 connected extra corporeally to a patient as an LVAD. The LVAD 200 connects to an outflow cannula 202, which is surgically connected to the left ventricle of the heart 208. The LVAD 200 also connects to an inflow cannula 204, which is surgically connected to the aorta 206. The LVAD 200 is maintained outside of the patient's body. The outflow and inflow cannulae 202, 204 enter the patient at openings 210, and extend up to the left ventricle 208 and the aorta 206, respectively.

FIG. 2B is a schematic illustration of a VAD 220 connected extra-corporeally to a patient as an RVAD. The RVAD 220 connects to an outflow cannula 222, which is surgically connected to the right atrium 224. The RVAD 220 is also connected to an inflow cannula 226, which is surgically connected to the pulmonary artery 228. The outflow and inflow cannulae 222, 226 enter the body at opening 230, and extend up to the right atrium 224 and the pulmonary artery 228, respectively.

FIG. 2C is a schematic illustration of two VADs 240a, 240b connected extra-corporeally to a patient as a BIVAD. The first VAD 240a is connected to an outflow cannula 242a, which is surgically connected to the right atrium of the heart 224. The first VAD 240a is also surgically connected to an inflow cannula 244a, which is surgically connected to the pulmonary artery 248. The second VAD 240b is connected to an outflow cannula 242b, which is connected to the left ventricle of the heart 208. The second VAD 240b is also connected to an inflow cannula 244b, which is connected to the aorta 252. The BIVADs 240a, 240b are maintained outside the patient's body and assist the right atrium and the left ventricle, respectively, of the heart 208, 224 by combining operation of both an RVAD and an LVAD. The cannulae 242a, 244a, 242b, 244b, may enter the patient's body at openings 256, 258, respectively, in the patient's chest.

At some time before, during, or after the surgery, surgeons must connect a cardiac circulatory support device, such as the VADS shown in FIGS. 1A through 2C, to the cannulae that are connected to the patient's heart. This connection requires a connector that is precisely adapted to the cannulae to reduce turbulence in the blood flow in the cardiac circulatory support system, avoids fluids draining from the inside of the cardiac circulatory support system, and also avoids the introduction of air or other undesired gasses into the cardiac circulatory support system. During the process of making the connection, the air volume in the cannulae can be replaced by saline solution, blood, or any other acceptable liquid. In general, saline solutions are any sterile solution of sodium chloride in water. These saline solutions are available in various formulations, for different purposes, such as intravenous infusion, rinsing contacts lens, and nasal irrigation.

The elimination of any air residue inside the cannulae or any part of the cardiac circulatory support system is necessary because the introduction of air bubbles, i.e., air embolisms, into the patient's circulatory system may result in serious complications. For example, air bubbles can block or occlude the blood vessels in the brain, thereby causing the loss in function of one or more parts of the body. Larger volumes of air may also result in venous air embolism, hypotension or dysrhythmias, or even death, when the air intake is rapid. Another risk is a pulmonary embolus occlusion, which is the blockage of an artery in the lungs by an air embolism. The air embolism results in an increase of dead space. Such a blockage could result in pulmonary constriction.

Large and rapid volumes of air entering into the blood stream may fill the right auricle and produce an air restriction that could result in the closing of the right ventricle, venous return diminution, and cardiac diminution. Myocardial ischemia and cerebral ischemia may then set in shortly.

In some cases, even if air replacement has been adequately and carefully performed, air bubbles may get trapped and remain inside the cannulae. Standard attempts to remove the trapped air bubbles involve extracting the bubbles with a syringe or by slapping the cannulae. Both methods are often time-consuming and somewhat imprecise.

Several types of apparatus and methods have been developed for purging unwanted fluids from a closed circulatory system. However, these apparatus and methods are typically excessively complex for simple applications, such as the purge of cannulae during a surgical procedure.

In addition, the connection itself may create problems during the connection of the cannulae to a VAD. Different cannulae and medical tube connectors have been developed to address such problems. However, they are typically excessively complex solutions for simple applications, such as connections to medical terminals. In addition, existing designs for securing the connections and for preventing the components from relative movement during operation generally mitigate against providing purging options for the connections. And certain purging methods make it more difficult to make the connection in a vertical position to a VAD in closed circulatory system.

Thus, there is a need for improved systems and methods for connecting cannulae to a blood pump that have the ability to purge air from the blood or other liquid inside the cannulae and elsewhere throughout the cardiac circulatory support system.

A disposable purging ("DIP") device for connecting cannulae to cardiac circulatory support devices for use in cardiac circulatory support system id disclosed. The DIP device is operable to purge air bubbles from the cannulae and from the cardiac circulatory support system and also to prevent the entry of air into the cardiac circulatory support system. The DIP device may include a device body having a distal ending and proximal ending, with an inner semi-closed flexible ring positioned towards the distal ending of the device body, and an air outlet having an external conduit extending radially from the device body.

A method of using such a DIP device connect cannulae to a cardiac circulatory support device is also disclosed. In one example method of operation, DIP devices in accordance with the invention are attached to the inflow and output ports of a ventricular assist devices ("VAD") and the VAD/DIP devices assembly is filled with a liquid, such as a saline solution. Each of the DIP devices are then alternatively occluded and filled with additional liquid to expel any air tapped in the assembly. Once this is completed, the VAD/DIP device assembly is maneuvered to allow for the insertion of the cannulae into the assembly while filling the cannulae and the assembly with the liquid. After the purging of any air in the DIP devices, the cannulae are inserted further into the assembly and connected to the VAD and the DIP devices are then removed from the VAD/cannulae assembly.

Other system, methods and features of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood with reference to the following figures. The components in the figures are not necessarily to scale, emphasis instead being placed upon illustrating the principles of the invention. In the figures, like reference numerals designate corresponding parts throughout the different views.

FIG. 2A shows a schematic illustration of a VAD in use extracorporeally with a patient as an LVAD.

FIG. 2B shows a schematic illustration of a VAD connected extracorporeally to a patient as a RVAD.

FIG. 2C shows a schematic illustration of two VADs connected extracorporeally to a patient as a BIVAD.

FIG. 5A shows a cross-sectional view from the distal ending of the example DIP device shown in FIG. 3.

FIG. 5B shows a cross-sectional view along line A-A in FIG. 5A.

DETAILED DESCRIPTION

In the following description of examples of implementations, references is made to the accompanying drawings that form a part hereof, and which show, by way of illustration, specific implementations of the invention that may be utilized. Other implementations may be utilized and structural changes may be made without departing from the scope of the present invention.

Figure 3:
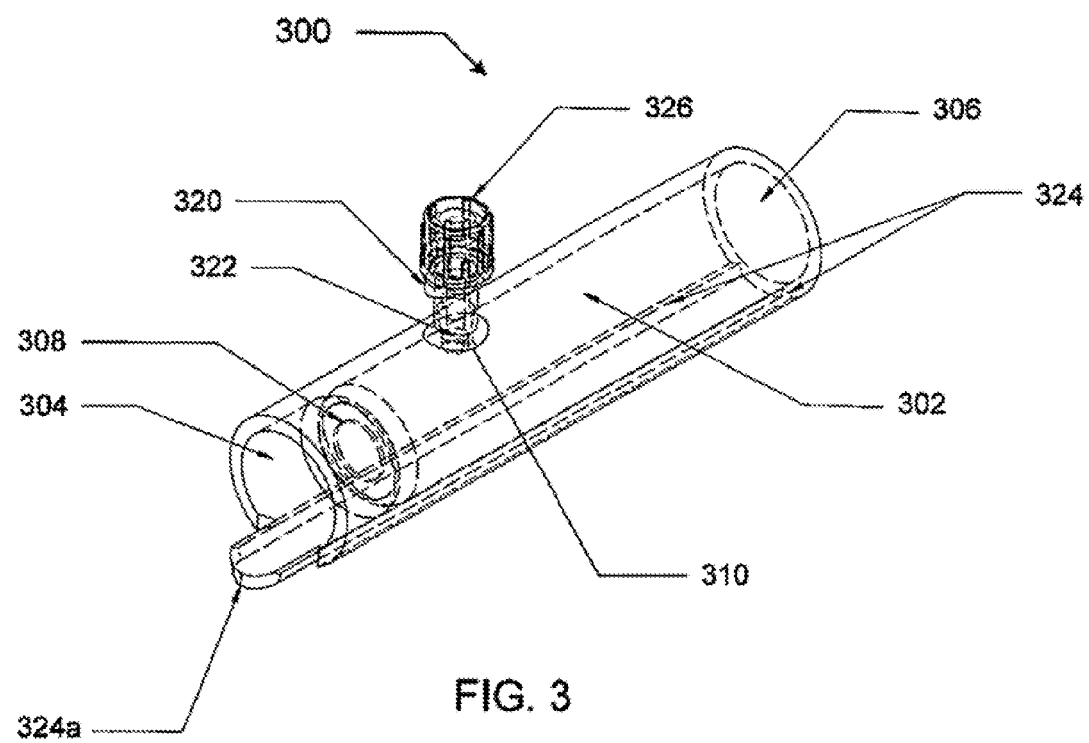
FIG. 3 shows a transparent perspective view of an example of a disposable purging ("DIP") device for connecting cannulae to a cardiac circulatory support device according to the present invention.

FIG. 3 shows a transparent perspective view of an example of a disposable purging ("DIP") device 300 for connecting cannulae to cardiac circulatory support devices operable to purge air bubbles from the cannulae and from the cardiac circulatory support system and also to prevent the entry of air into the cardiac circulatory support system. FIG. 2 shows an exploded perspective view of the device of FIG. 3 that illustrates how the components of the DIP device 300 are configured relative to each other.

The DIP device 300 includes a device body 302 having a distal ending 304 and a proximal ending 306. The device body 302 may include an inner semi closed flexible ring 308 positioned towards the distal ending 304 of the device body 302, and an air outlet 310. An external conduit 322 extending radially from the device body 302 between the distal ending 304 and the proximal ending 306 is connected or linked to the air outlet 310. A female plug 320 may be inserted into the external conduit 322, with a male plug 326 coupled to or capping the female plug 320 so as to permit control of the opening and closing of the air outlet 310 at the external conduit 322. The device body 302 includes a detachment section 324 to permit removal of the DIP device 300 from a connected and air-bubble-free assembly of medical tubing and cardiac circulatory support devices. The detachment section 324 may include a flap 324A that extends beyond the distal ending 304 to provide a portion of the detachment section 324 on which the user may grasp the detachment section 324 to allow for pulling off and disconnecting the DIP device 300.

Figure 4:
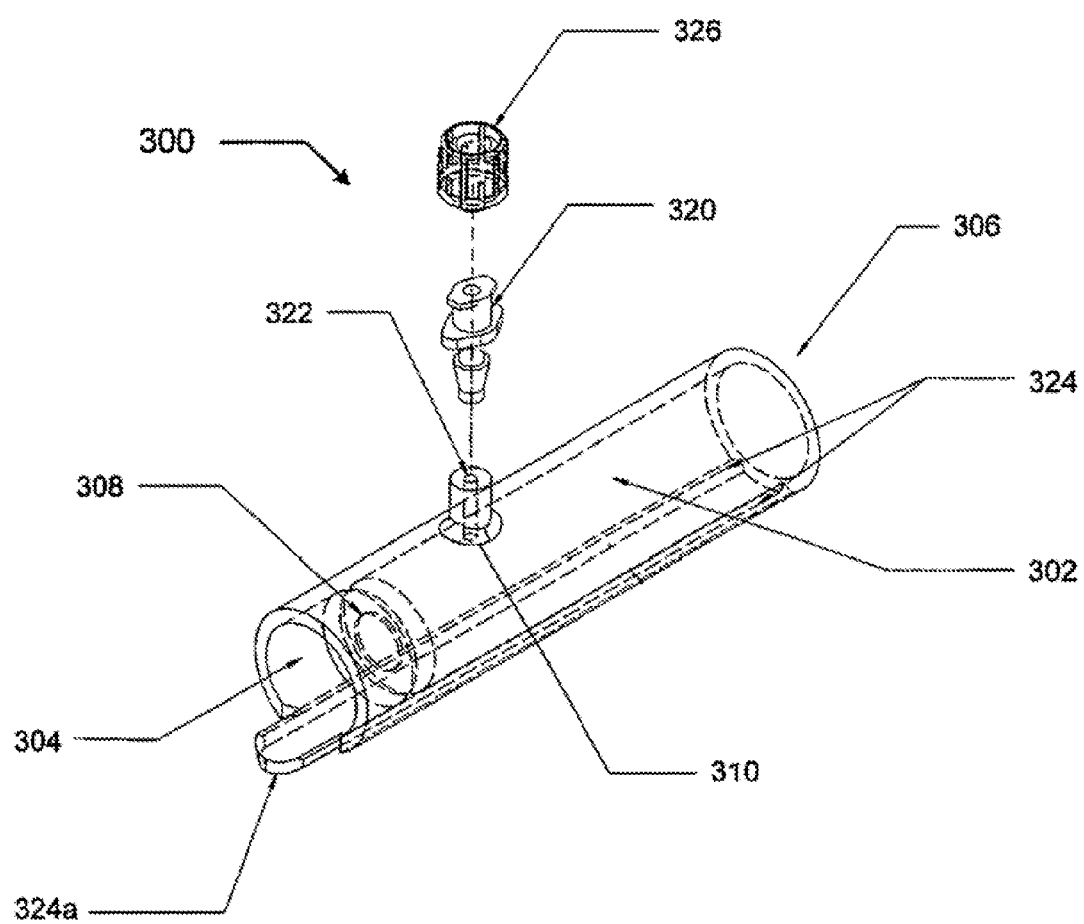
FIG. 4 shows a transparent exploded perspective view of the example DIP device shown in FIG. 3.

The device body 302 generally conforms to the shape of the tubes making up the closed fluidic circuit in which the device 300 is used. The example device body 302 shown in FIGS. 3 and 4 is a hollow, flexible, and transparent or translucent tubular body, and may be made of a natural or synthetic elastomeric or polymeric material. The device body 302 is hollow inside, having openings at the distal ending 304 and the proximal ending 306. The proximal ending 306 connects to a circulatory support device, which may be a blood pump or a ventricular assist device ("VAD"), or any other type of pump or device used for circulatory support. The distal ending 304 connects to a cannula or other type of medical tubing utilized in medical applications. The device body 302 may also be configured to be occluded at any part of its body with clamps or other similar surgical instruments. Moreover, the length of the device body 302 may be easily modified by cutting or tearing the body transversely, so as to obtain a shorter or longer device body 302, as the case may be, in order to facilitate the connection of cannulae to the cardiac circulatory support device.

The DIP device 300 of FIG. 3 may be used to connect medical tubing, such as cannulae, that may be surgically implanted in a patient for connection to a cardiac circulatory support device. The DIP device 300 facilitates connection of the cannulae to the cardiac circulatory support device. Once connected, the DIP device 300 also allows its users to purge any air bubbles that may have former in the liquid flowing through the cardiac circulatory support device during the connection. Typical cardiac circulatory support devices include an inflow port to receive fluid such as blood, and an outflow port through which blood flows out of the cardiac circulatory support device. The cardiac circulatory support device may pump the blood or other liquid it receives at the inflow port through the outflow port for circulation through the patient's body. One cannula may be implanted into the patient to carry blood that will flow to the cardiac circulatory support device and another cannula may be surgically implanted into the patient to carry blood from the cardiac circulatory support device at the outflow port back to the patient. During connection of the cannulae to the cardiac circulatory support device, one DIP device 300 receives one cannula at the distal ending 304. The proximal ending 306 is connected to one of the ports of the cardiac circulatory support device. Another DIP device 300 is used to connect the other cannula to the other port of the cardiac circulatory support device.

The inner semi-closed flexible ring 308 is positioned in the inner surface of the device body 302. The inner semi-closed flexible ring 308 may be made of natural or synthetic elastomeric or polymeric material, and may be attached by adhesive, welding, or other suitable attachment method. The inner semi-closed flexible ring 308 may also be molded as part of the device body 302. The inner semi-closed flexible ring 308 includes an opening sufficient to permit insertion of the cannula. The opening is also sufficiently snug around the surface of the cannula to seal, thus avoiding the entry of air into device 300 during the insertion of the cannula to seal, thus avoiding the entry of air into the device 300 during the insertion of the cannula. This seal where the cannula contacts the semi-closed flexible ring 308 separates the liquid inside the cannula and the device 300 from the air outside the cannula and the DIP device 300.

The external conduit 322 may be connected or linked to the air outlet 330 formed in the device body 302. The external conduit 322 may be made of natural or synthetic elastomeric or polymeric material. The external conduit 322 may be filled with a female plug 320, which may be formed to permit the insertion of a syringe for extracting fluid and air bubbles from the DIP device 300. In one example, the female plug 320 may be a female luer-type plug, and may be fixed to the external conduit 322 by adhesive or other fixing means. The female plug 320 may also be manufactured, for example, by molding the female plug 320 and the external conduit 322 with the device body 302 as a single unit. The external conduit 322 may also include a male plug 326 which may be used to cover the female plug 320 or as a tap to control the inflow and outflow of liquids through the connecting device 300. In one example implementation, the male plug 326 may be a male luer-type that may lock in with the female lure-type plug 320 to allow for selective sealing and opening of the outlet 310 in the device body 302.

The detachment section 324 of the device body 302 may be formed with two seams that run parallel along the length of the device body 302. The seams are formed to allow the user to tear the detachment section 324 from the rest of the device body 302. The flap 324a extends from the detachment section 324 to provide a grip to case the act of pulling the detachment section 324 from the device body 302. The detachment section 324 may be made of metallic or polymeric material, or any other material that may provide a seal with the remainder of the device body 302, yet permit easy removal of the detachment section 324 from the device body 302.

FIG. 5A shows a front view from the distal ending 304 of the DIP device 300 of FIG. 3. The view in FIG. 5A shows the semi-closed flexible ring 308, the external conduit 322, the female plug 320, the male plug 326, and the detachment section 324. The detachment section 324 is shown in FIG. 3A as that section of the device body 302 between two notches or cuts where the device body 302 is thinner than the rest of the device body 302.

FIG. 5B shows a cross-sectional view of the DIP device 300 at line A-A shown in FIG. 5A. FIG. 5B shows flap 324a extending from the detachment section 324 that allows user to grasp the flap 324a and pull the detachment section 324 from the device body 302, thus allowing removal of the DIP device 300 from a cannulae/VAD assembly. Other means for tearing or separating the device body 302 may be used to allow removal of the DIP device 300 once the cannulae have been connected to cardiac circulatory support device.

The DIP device 300 may be used to connect a cardiac circulatory support device to a patient. The cardiac circulatory support device may be a VAD, a blood pump, or any other type of pump or device used for pumping blood or other liquid during a procedure requiring circulatory support. The examples described below refer to the use of DIP devices in the context of connecting cannulae to a VAD. However, it is to be understood that reference to a VAD is purely for purposes of providing a description and is not intended as any kind of limitation. Examples of VADs that may be used in the examples described below are described in U.S. Pat. No. 7,217,236 to Calderon et al., issued May 15, 2007, which is incorporated herein by reference in its entirety.

Figure 6A:
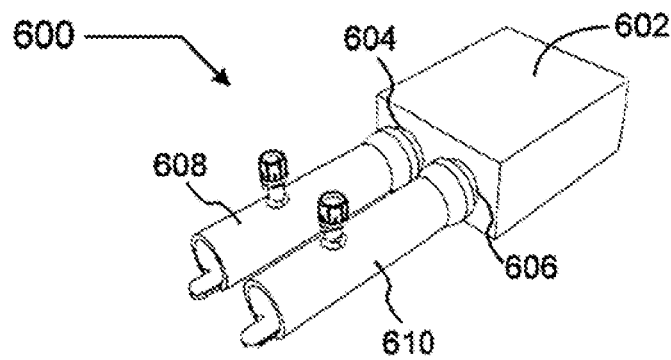
FIGS. 6A and B illustrate an example of utilizing a DIP device in accordance with the invention to connect cannulae to a cardiac circulatory support device.
Figure 6B:
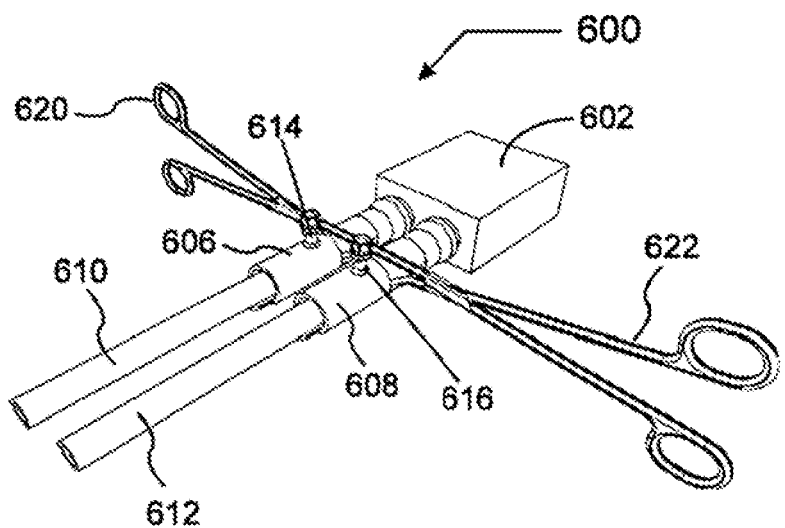

FIGS. 6A and 6B illustrate an example of utilizing a DIP device to connect cannulae to a cardiac circulatory support device. FIG. 6A shows a VAD 602 connected to a pair of DIP devices 608, 610. The VAD 602 includes an inflow connector 604 and an outflow connector 606. The first DIP device 608 is connected to the inflow connector 604 and the second DIP device 610 is connected to the outflow connector 606.

Referring to FIG. 6A, a VAD/DIP device assembly 600 is formed by connecting the first DIP device 608 to the input connector 604 of the VAD 602, and the second DIP device 610 to the output connector 606 of the VAD 602. The assembly 600 may then be filled with a liquid, such as a saline solution, and any air bubbles removed via the distal openings of the DIP devices 608, 610. As described in further detail with reference to FIGS. 10-15B below, the liquid is added at the distal ending of the DIP devices 608, 610 while the assembly 600 is oriented with the distal endings pointing up. The VAD 602 is thus positioned so as to collect the liquid being poured into the assembly. Once the assembly 600 shown in FIG. 6A is filled with the liquid, any air bubbles mat be removed via the opening at the distal endings of the DIP devices 608, 610.

FIG. 6B shows the VAD 602 connected to the two DIP devices 606, 608 and to cannulae 610, 612, which are inserted into corresponding DIP devices 606, 608. The DIP devices 606, 608 are occluded using a pair of clamps 320, 622, respectively. The two cannulae 610, 612 may then be surgically implanted into the patient. While filling the cannulae 610, 612 and the DIP devices 606, 608 with liquid, the cannulae 610, 612 are inserted into the DIP devices 606, 608, respectively. The ends of the cannulae 610, 612 may be held in the body of the DIP devices 606, 608 by the inner semi-closed flexible ring 108, FIG. 1. The cannulae 610, 612, the DIP device 606, 608 and the VAD 600 may thus form a closed container of liquid. Any trapped air bubbles may be removed via the external radially-disposed conduits 614, 616 on the DIP devices 606, 608, respectively.

Figure 7:
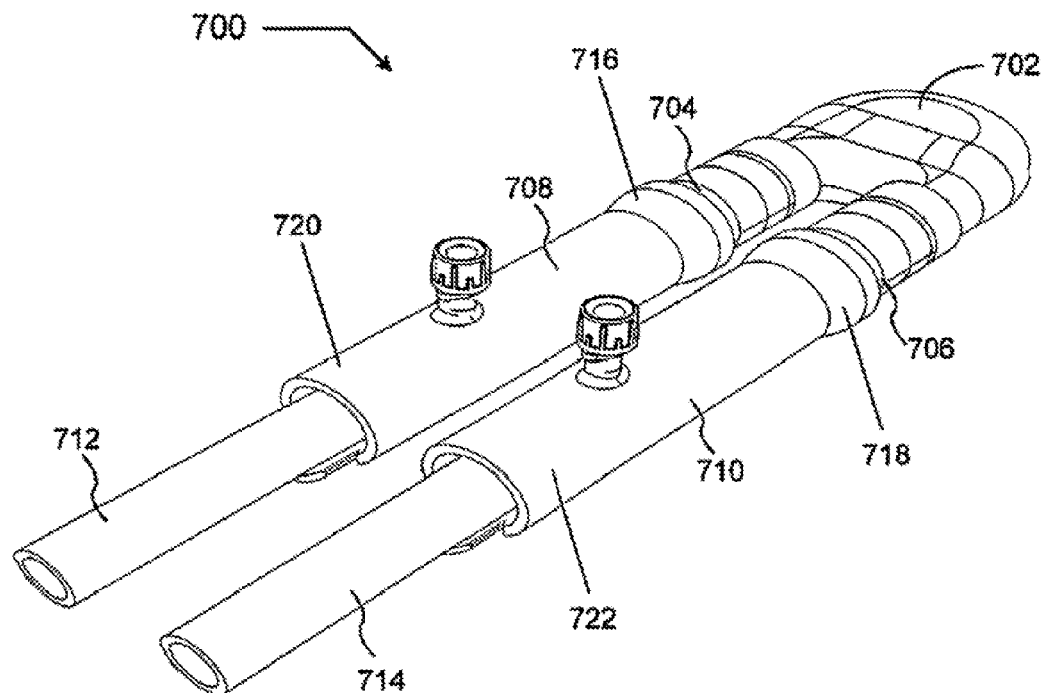
FIG. 7 shows a perspective view of an example assembly that includes an example DIP device in accordance with the invention, two cannulae and a VAD.
Figure 8:
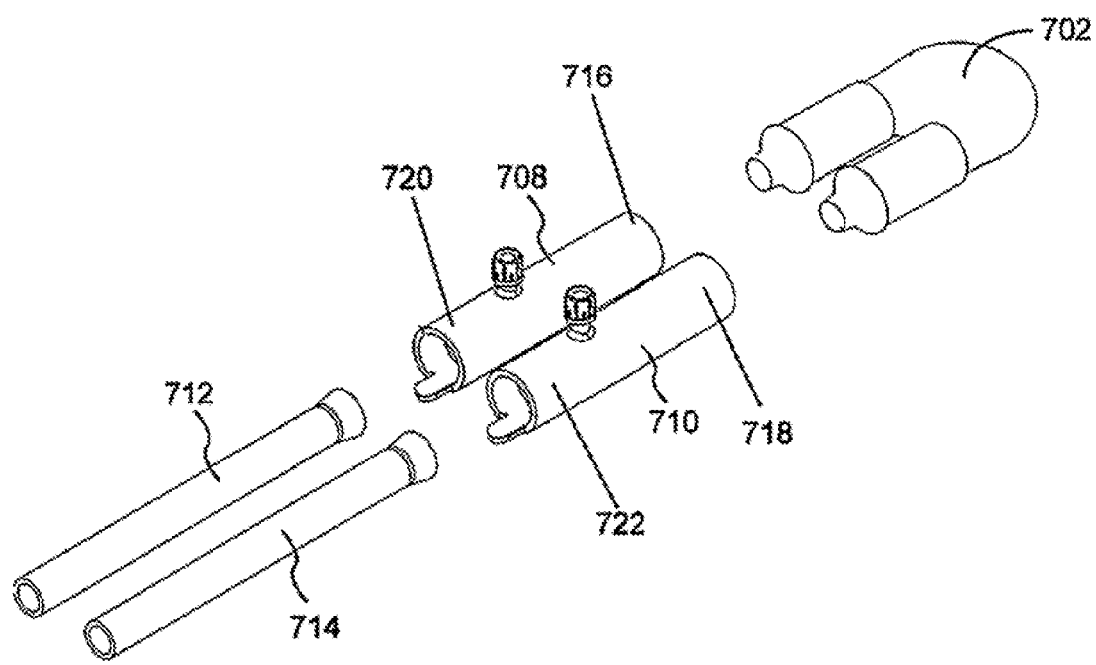
FIG. 8 shows an exploded perspective view of the assembly shown in FIG. 7.
Figure 9:
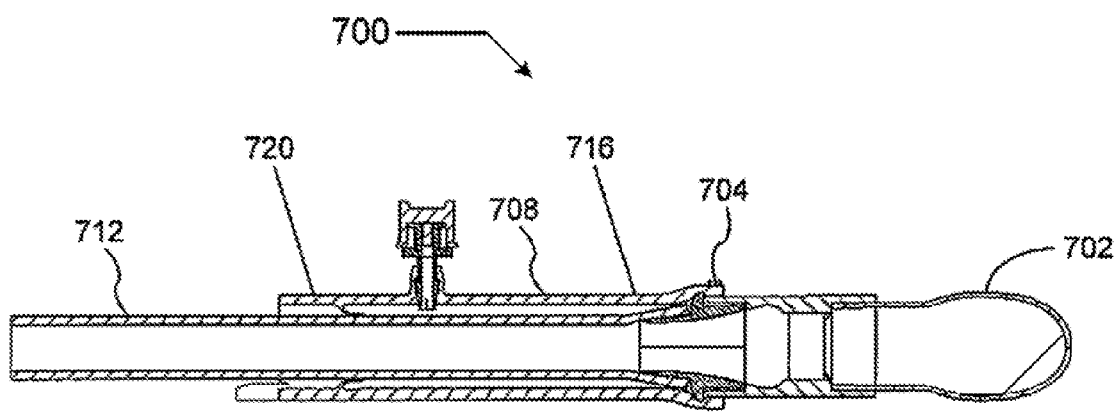
FIG. 9 shows a longitudinal cross-sectional view of the assembly shown in FIG. 7

FIG. 7 is a perspective view of an example assembly ("VAD/DIP device/cannulae assembly") 700 that includes two DIP devices 708, 710, two cannulae 712, 714 and a VAD 702. FIG. 8 shows an exploded perspective view of the assembly in FIG. 7 illustrating how the components fit with one another. FIG. 9 shows a longitudinal cross-sectional view of the assembly shown in FIG. 7, which also illustrates how the components fit with one another. Referring to FIGS. 7, 8 and 9, the two DIP devices 708, 710 are connected to the VAD 702 via respective connectors that include the input connector 704, which connects to the proximal ending 716 of the first DIP device 708, and the output connector 706, which connects to the proximal ending 718 of the second DIP device 710. The two cannulae 712, 714 are shown inserted into the DIP devices 708, 710 at the distal endings 720, 722, respectively.

FIGS. 10-29B illustrate how examples of a DIP device in accordance with the invention may be used to connect annulae that have been surgically attached to a patient to a cardiac circulatory support device. The illustrated examples depict attachment to a VAD; however, similar procedures may be used for other cardiac circulatory support devices.

Figure 10:
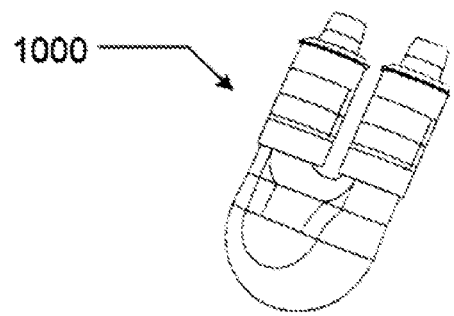
FIG. 10 shows a perspective view of an example VAD that may be used in the assembly shown in FIG. 8.
Figures 11A, 11B:
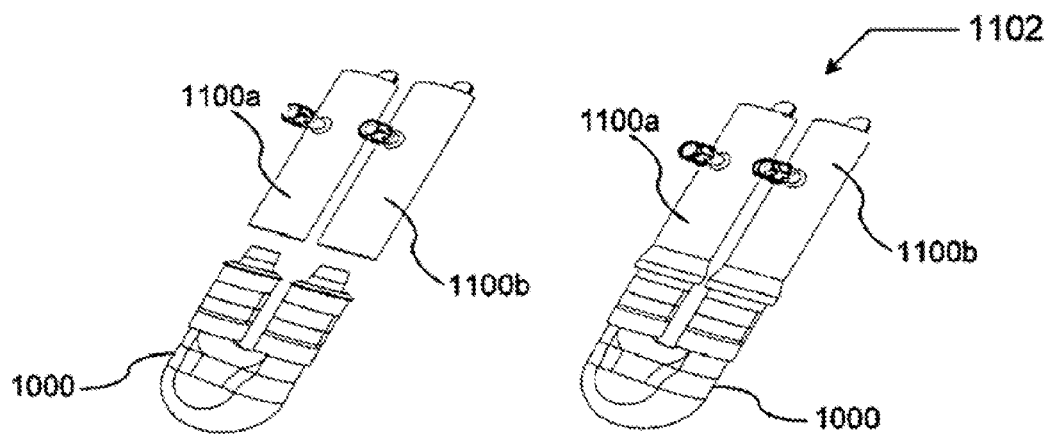
FIGS. 11A and 11B illustrate attachment of DIP devices in accordance with the invention to the example VAD of FIG. 10.

FIG. 10 is a perspective view of an example VAD 1000 that may be used in a VAD/DIP device/cannulae assembly such as that shown in FIG. 7. FIGS. 11A and 11B illustrate attachment of two DIP devices 1100a, 1100b to the example VAD 1000 of FIG. 10. The DIP devices 1100a, 1100b may be attached by an air-tight seal, which may be formed by a tight fit of the elastic material of the DIP devices 1100a, 1100b around the inflow and outflow ports of the VAD 1000, respectively. An air-tight seal, may also be formed using a clamp or other conventional scaling methods. The VAD 1000 and attached DIP devices 1100a, 1100b, once assembled, form a VAD/DIP device assembly 1102 as shown in FIG. 11B.

Figures 12A, 12B:
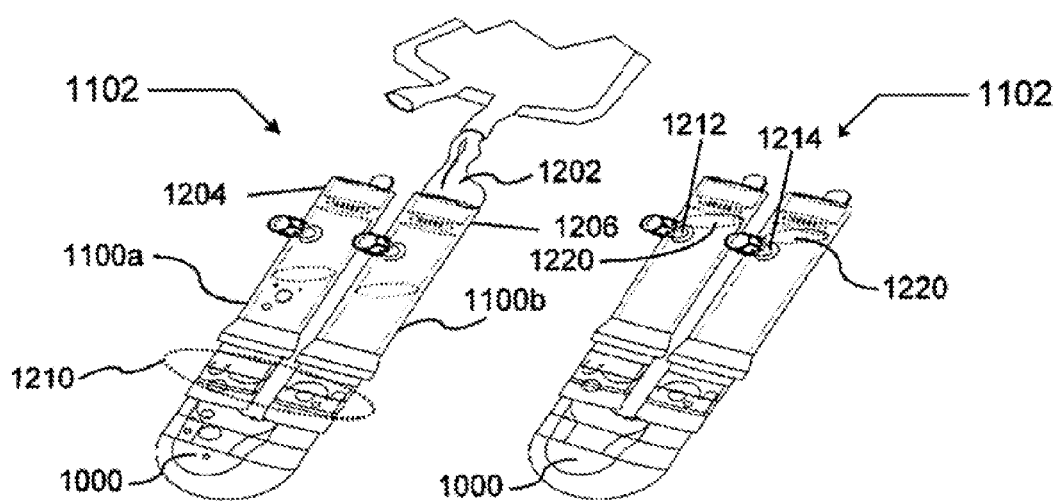
FIGS. 12A and 12B illustrate adding a liquid to the VAD/DIP device assembly in FIG. 11B.
Figure 13:
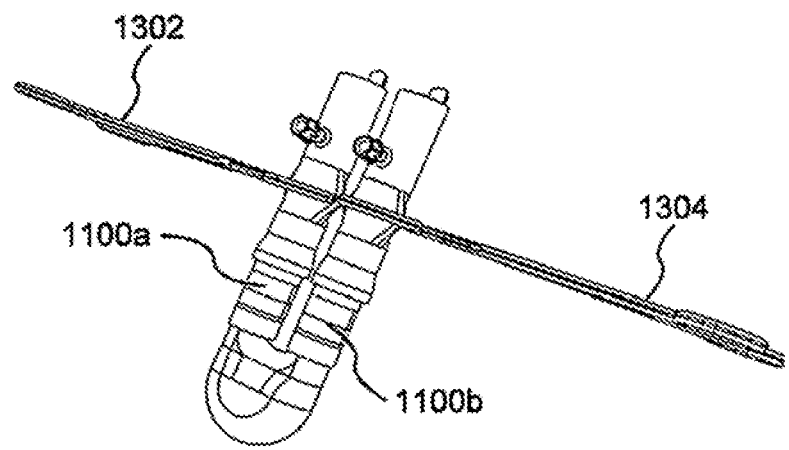
FIGS. 13 and 14 illustrate the DIP devices and turning the VAD/DIP device assembly upside-down.

FIGS. 12A and 12B illustrate adding a liquid 1202 to the VAD/DIP device assembly 1102 of FIG. 11B. The liquid 1202 may be added to the distal openings 1204 and 1206 of either of the respective DIP devices 1100a, 1100b as shown in FIG. 12A. As the liquid 1202 is poured into the VAD/DIP device assembly 1102, the liquid 1202 replaces the air inside the VAD/DIP device assembly 1102. However, air bubbles 1210 may remain or form inside the VAD/DIP device assembly 1102. The liquid 1202 is added to the VAD/DIP device assembly 1102 until the liquid level 1210 in each DIP device 1100a, 1100b is above the air outlet at the external conduit 1212, 1214, which may be closed by the engagement of a male lock plug in a closed position. While the liquid 1202 is being added, the VAD/DIP device assembly 1102 must kept in the upright, vertical position, with the distal endings up. With the level 1220 of the liquid 1202 inside the VAD/DIP device assembly 1102 as shown in FIG. 12B,m the DIP devices 1100a, 1100b may then be occluded below the air outlet at the external conduits 1212, 1214, respectively, to close the container of liquid.

Figure 14:
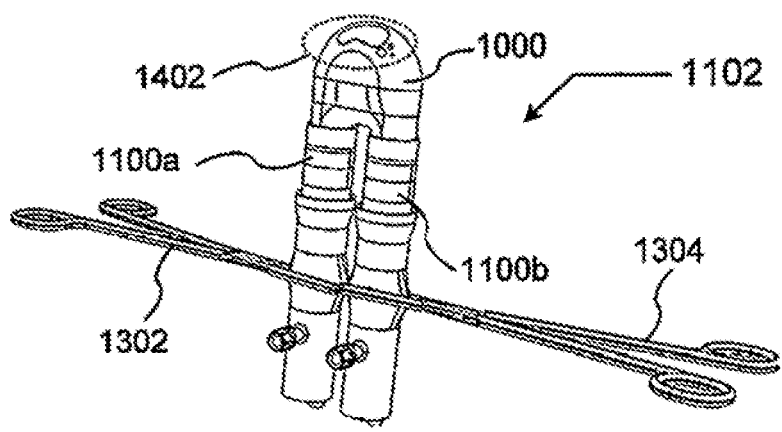

Turning to FIG. 11 this figure illustrates occluding the DIP devices 1100a, 1100b using a pair of clamps 1102 and 1104, respectively. FIG. 14 illustrates turning the closed VAD/DIP device assembly 1102 liquid container upside-down, causing any trapped air bubbles 1402 to collect in the VAD 1000. If necessary, the VAD/device assembly 1102 may be shaken or tapped to cluster or join the existing air bubbles 1402 in a single air bubble.

Figure 15A:
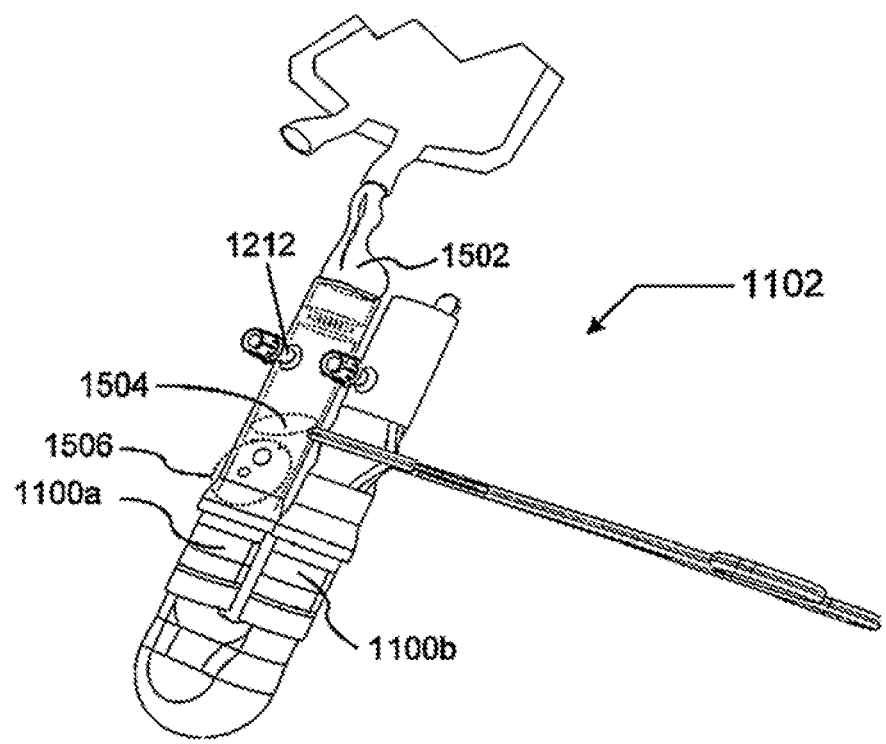
FIGS. 15A and 15B illustrate adding more liquid to the VAD/DIP device assembly.

The air bubbles once collected may then be moved back to one or both of the DIP devices 1100a, 1100b by turning the VAD/DIP device assembly 1102 back over so that the DIP devices 1100a, 1100b again point upwards, as shown in FIG. 14. When the VAD/DIP device assembly 1102 was turned upside down in FIG. 14, the liquid contained in the space between the clamps 1102 and 1104 and the proximal openings of the DIP devices 1100a, 1100b empties out of the DIP devices 1100a, 1100b. FIG. 15A illustrates removal of the clamp 1102 (not shown) from the first DIP device 1100a to permit the addition of more liquid 1502 to the VAD/DIP device assembly 1102. The liquid 1502 may be added to the first DIP device 1100a until the liquid level 1504 rises above the air outlet at the external conduit 1212. As the liquid 1502 is added the air bubbles 1506 may be released at the open distal ending of the first DIP device 1100a. Once the liquid level 1504 has risen to a suitable level and air bubbles 1506 are released, the first DIP device 1100a may be occluded again with the clamp 1102 as shown in FIG. 11.

Figure 15B:
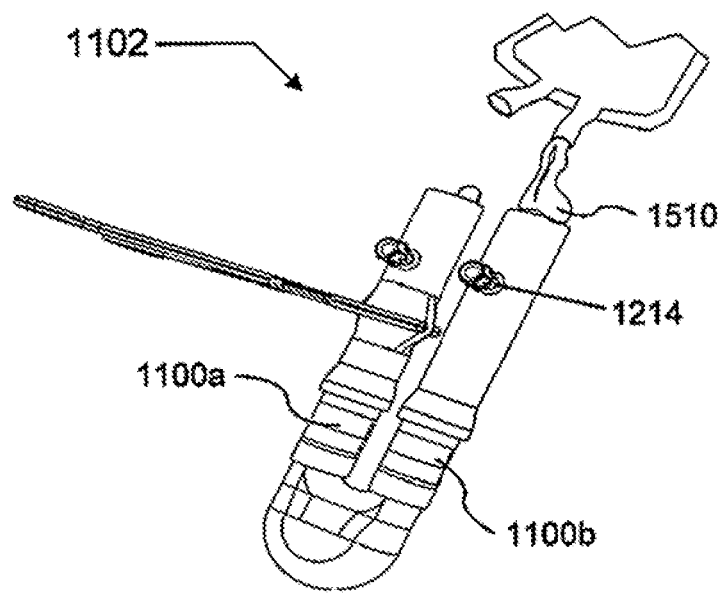

FIG. 15B illustrates the second DIP device 1100b without the clamp 1104, FIG. 11, that was scaling the liquid in the VAD/DIP device assembly 1102 from the space in the second DIP device 1100b. FIG. 15B illustrates adding more liquid 1510 to the second DIP device 1100b in the VAD/DIP device assembly 1102. The liquid is added as shown in FIG. 15B until the liquid level in the second DIP device 1100b rises to a suitable level above the external conduit 1214 of the second DIP device 1100b, and any trapped air bubbles are released at the distal ending opening of the second DIP device 1100b in the same manner as shown in FIG. 15A.

Figure 16:
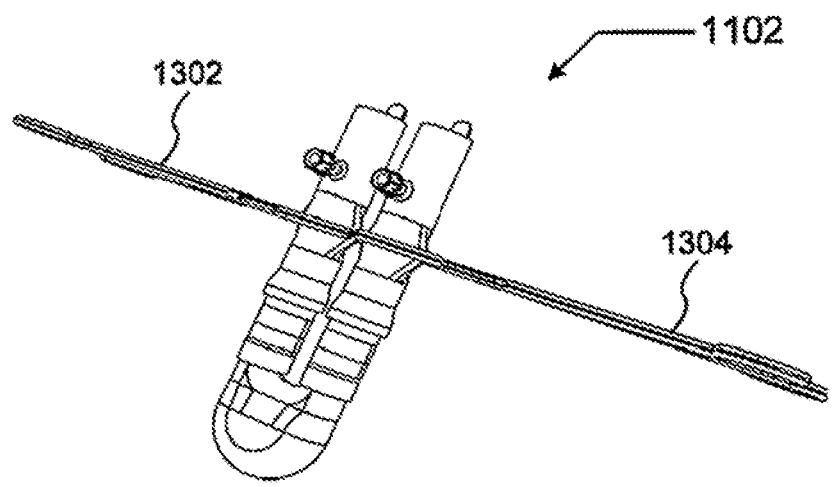
FIG. 16 shows the VAD/DIP device assembly clamped and filled with liquid prior to connection of the cannulae to the VAD.

This purging process of the second DIP device as well as the purging process of the first DIP device 1100a may be repeated as many times as necessary to achieve a liquid-filled, air bubble-free, VAD/DIP device assembly 1102. Turning to FIG. 16, this figure shows the VAD/DIP device assembly 1102 occluded with clamps 1102 and 1104, and ready for further manipulation, including the connection of cannulae to the VAD 1000. The VAD/DIP device assembly 1102 as shown in FIG. 16 is filled with a liquid and is also purged of any trapped air bubbles within the closed liquid container portion of the VAD/DIP device assembly 1102 between the two clamps 1102 and 1104.

Figure 17A:
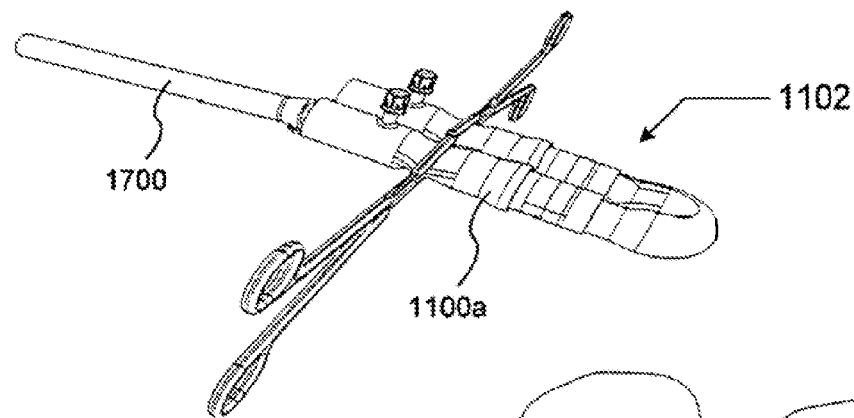
FIGS. 17A, 17B, and 17C illustrate connection of one of two cannulae, an outflow cannula, to the VAD/DIP device assembly.

In general, FIGS. 17A through 27 illustrate the connection of cannulae to the VAD/DIP device assembly 1102 of FIG. 17A and the purging of air bubbles from the resulting VAD/DIP device/cannulae assembly. FIGS. 17A, 17B, and 17C illustrate the connection of a first cannula 1700 to the VAD/DIP device assembly 1102 shown in FIG. 16. In FIG. 17A, the air-purged, bubble-free VAD/DIP device assembly 1102 is placed facing the distal ending of the first cannula 1700 so that the first cannula 1700 is in position for insertion into the first DIP device 1100a at its distal ending. The first cannula 1700 is an output cannula with reference to the patient's heart as this is always the cannula that is first connected to the VAD (and an input cannula with reference to the VAD). During the cannulae-VAD/connector assembly connection process, the VAD/DIP device assembly 1101 may be manipulated or handled in any position, including the vertical, while retaining its air-purged and bubble-free condition. Although the first cannula 1700 may be surgically attached to a patient (not shown) at an end of the cannula 1700, unrestricted, controllable movements in the cannulae-VAD/connector assembly connection process are still possible regardless of which connection method or cardiac circulatory support device may be used.

Figure 17B:
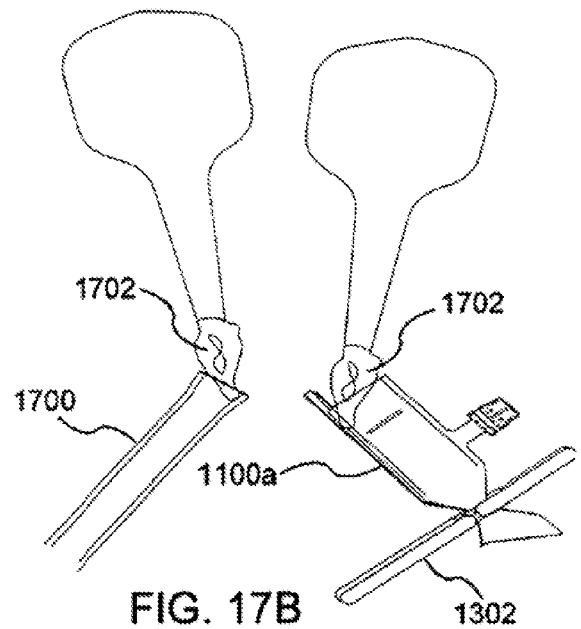
Figure 17C:
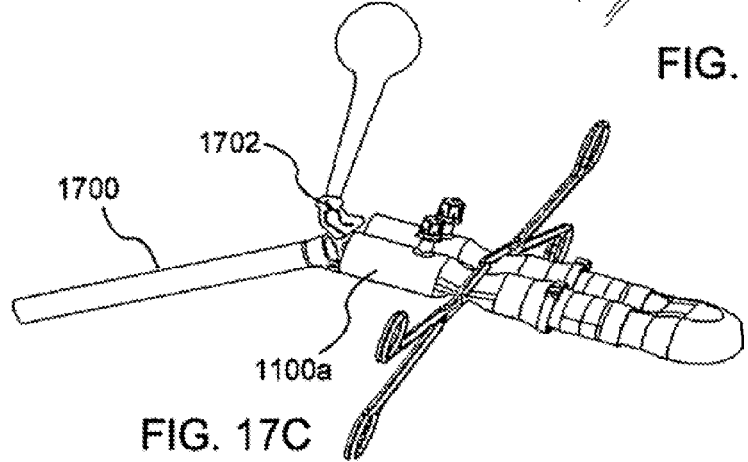

FIG. 17B illustrates adding a liquid 1702 to the first cannula 1700 and to the first DIP device 1100a while the first DIP device 1100a remains occluded by clamp 1102. In FIG. 17C, the liquid 1702 is added to both the first cannula 1700 and the first DIP device 1100a as the open end of the first cannula 1700 and the distal ending of the DIP device 1100a a are placed in close proximity to one another. The liquid 1702 is poured into both as the cannula 1700 is inserted into the first DIP device a. This minimizes the possibility of having air bubbles enter into the space inside the first DIP device 1100a.

Figure 18:
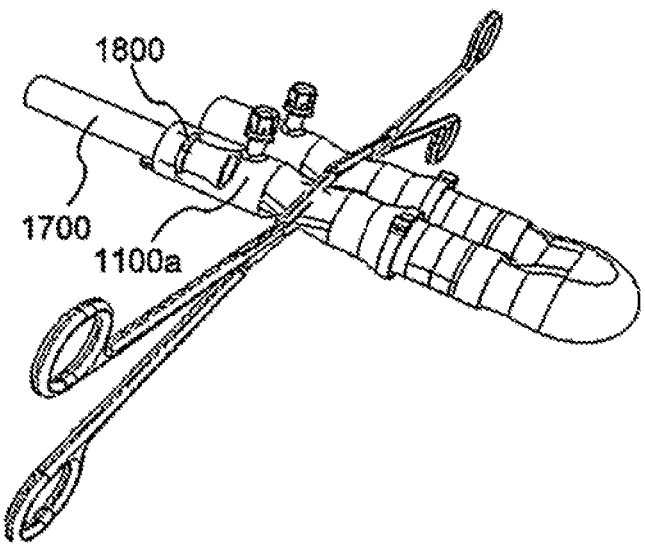
FIG. 18 illustrates the outflow cannulae inserted into the VAD/DIP device assembly.
Figure 19:
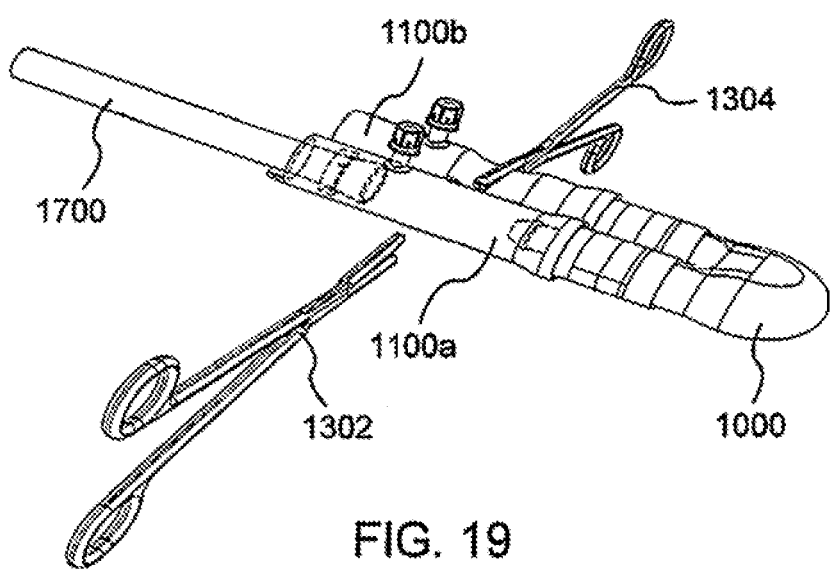
FIG. 19 illustrates removal of the clamp occluding the DIP device.
Figure 20:
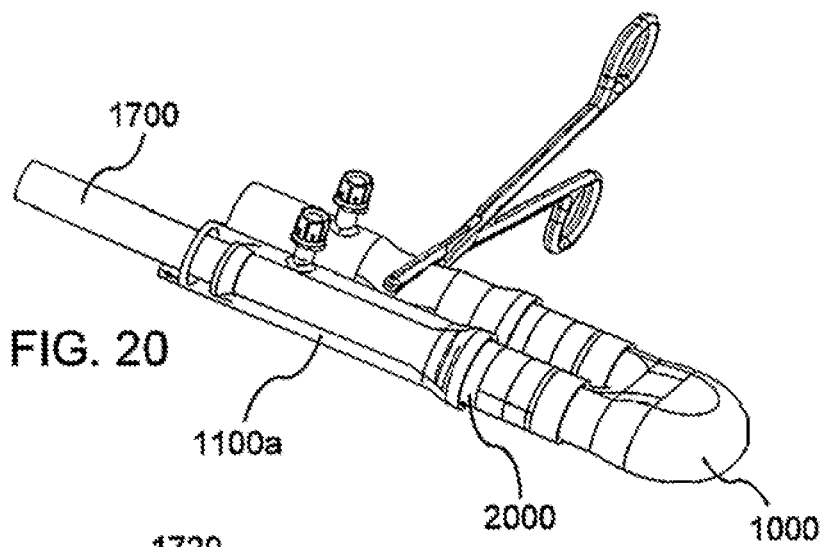
FIG. 20 illustrates connection of the inflow of the VAD to the outflow cannulae inserted at the distal ending of the inflow DIP device.

FIG. 18 illustrates the first cannula 1700 partially inserted into the first DIP device 1100a. The cannula 1700 is inserted until the end advances past the inner semi-closed flexible ring 1800. In FIG. 19, the clamp 1102 occluding the first DIP device 1100a is removed, creating a closed container of liquid in the first cannula 1700, the first DIP device 1100a, the VAD 1000, and the second DIP device 1100b up to the point at which the clamp 1104 creates the remaining occlusion. FIG. 20 illustrates further insertion of the first cannula 1700 into the first DIP device 1100a until a connection is established at connector 2000 with the inflow port of the VAD 1000.

Figure 21:
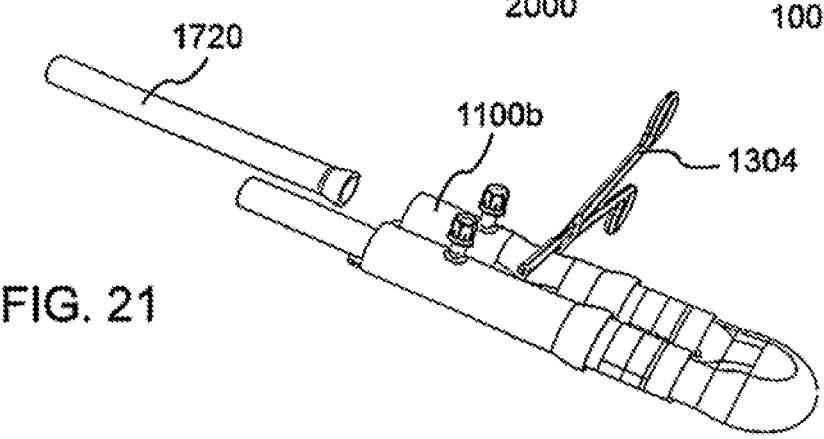
FIG. 21 shows the second cannulae, i.e., the inflow cannulae, prior to insertion into the DIP device that is still occluded.
Figure 22:
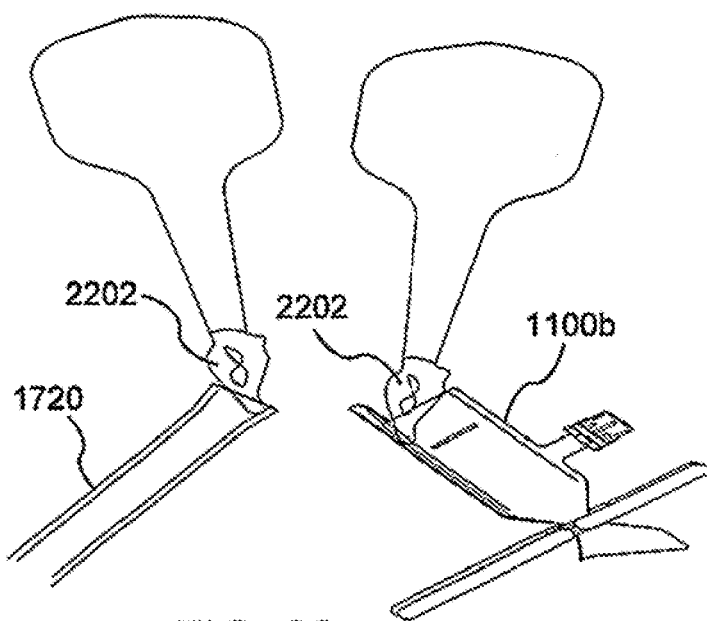
FIGS. 22, 23, and 24 illustrate connection of the inflow cannulae to the VAD/DIP device assembly.
Figure 23:
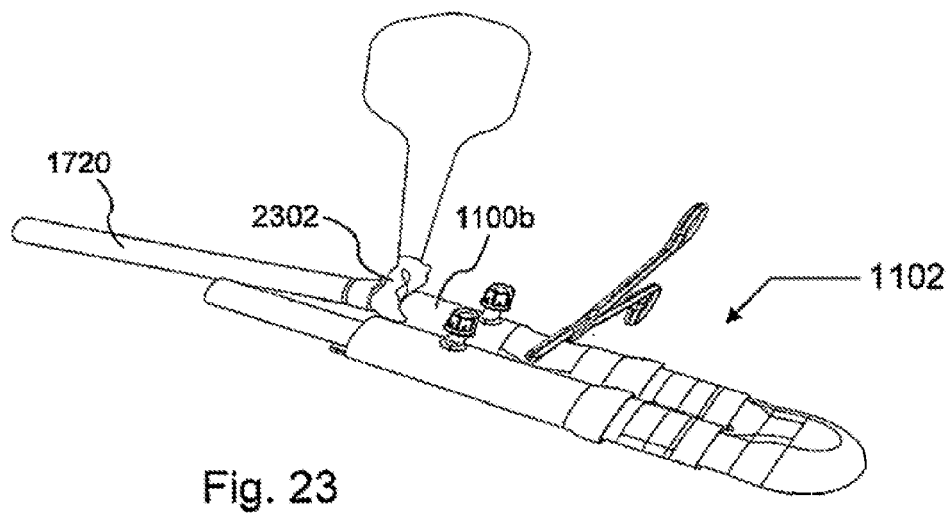
Figure 24:
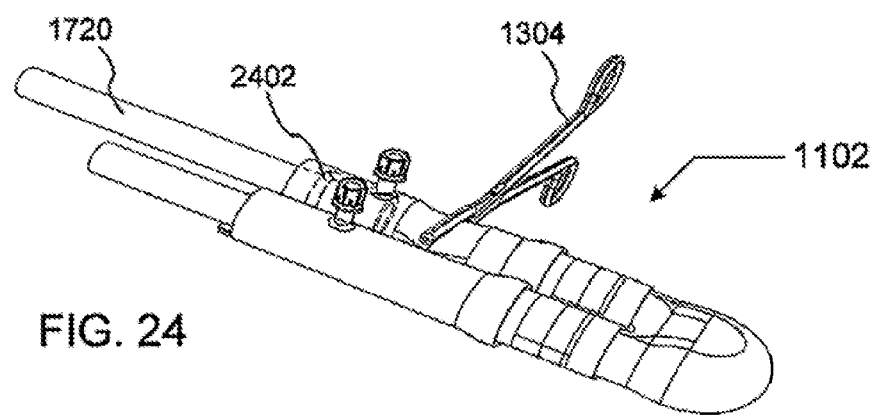

Once the outflow cannula is connected to the VAD/DIP device assembly and purged, the process must be repeated for the inflow cannula (with reference to the patient's heart). Turning to FIG. 21, a second cannula 1720 is shown prior to insertion into the second DIP device 1100b that is still occluded by the clamp 1104. FIG. 22 illustrates liquid 2202 being poured into the distal endings of the second cannula 1720 and the second DIP device 1100b. In FIG. 21, the liquid 2102 is being simultaneously poured into both the second cannula 1720 and the second DIP device 1100 as the second cannula 1720 is inserted into the second DIP device 1100b, thereby preventing the introduction of air into the VAD/DIP device assembly 1102. In FIG. 24, the second cannula 1720 is inserted into the VAD/DIP device assembly 1102 such that the tip of the second cannula 1720 moves beyond the inner semi-closed flexible ring 2402. Clamp 1104 remains in place, partially occluding VAD/DIP device assembly 1102.

Figure 1A:
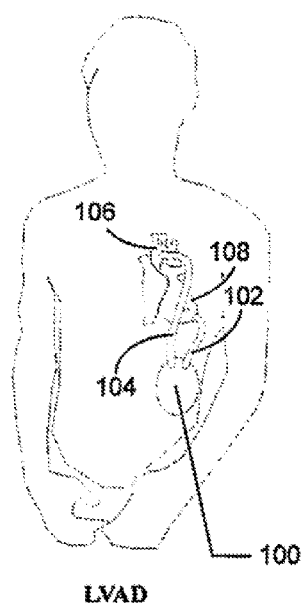
FIG. 1A shows a schematic illustration of a ventricular assist device ("VAD") implanted in a patient as a left ventricular assist device ("LVAD").
Figure 1B:
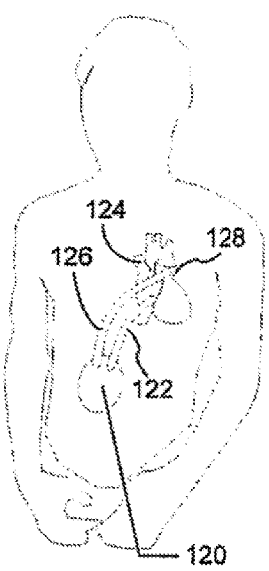
FIG. 1B shows a schematic illustration of a VAD implanted in a patient as right ventricular assist device ("RVAD").
Figure 1C:
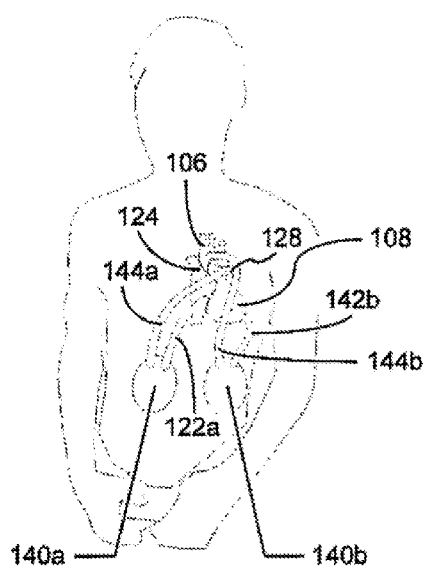
FIG. 1C shows a schematic illustration of two VADs implanted in a patient as a biventricular assist device ("BI-VAD").
Figure 25A:
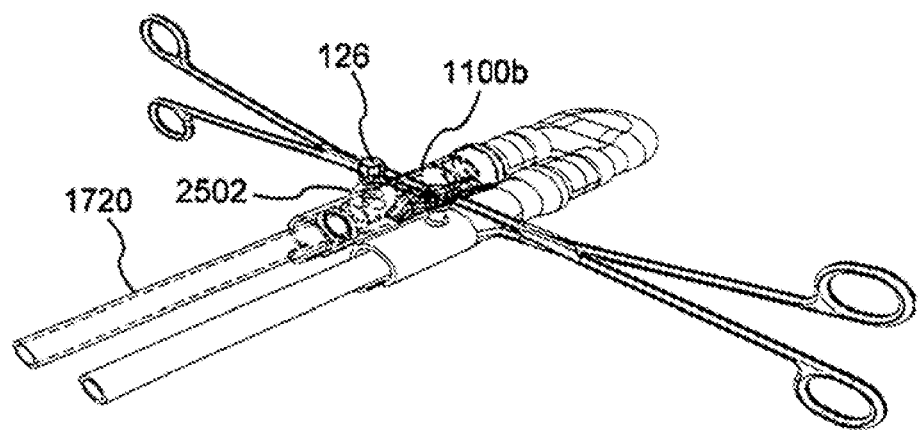
FIGS. 25A-25D illustrate an example of a method for removing air bubbles that entered the assembly during the insertion of the cannulae into the DIP devices.
Figure 25B:
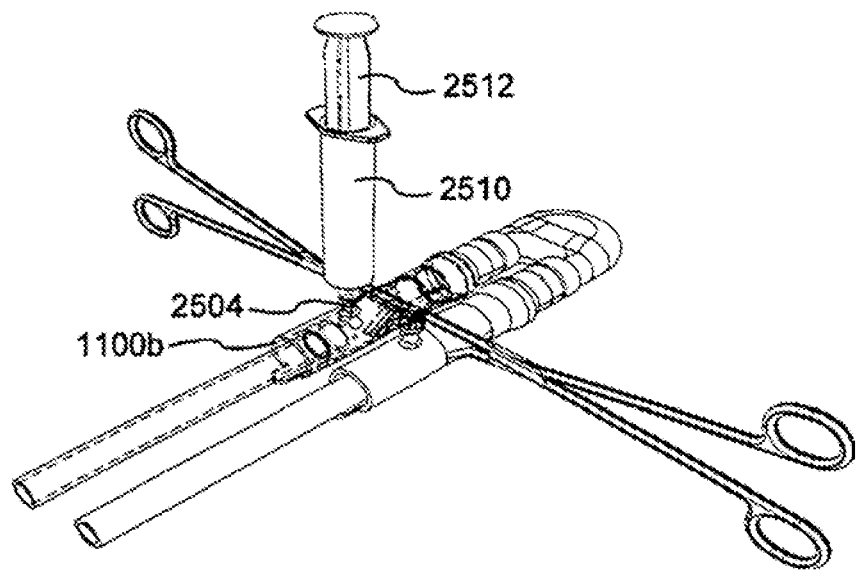
Figure 25C:
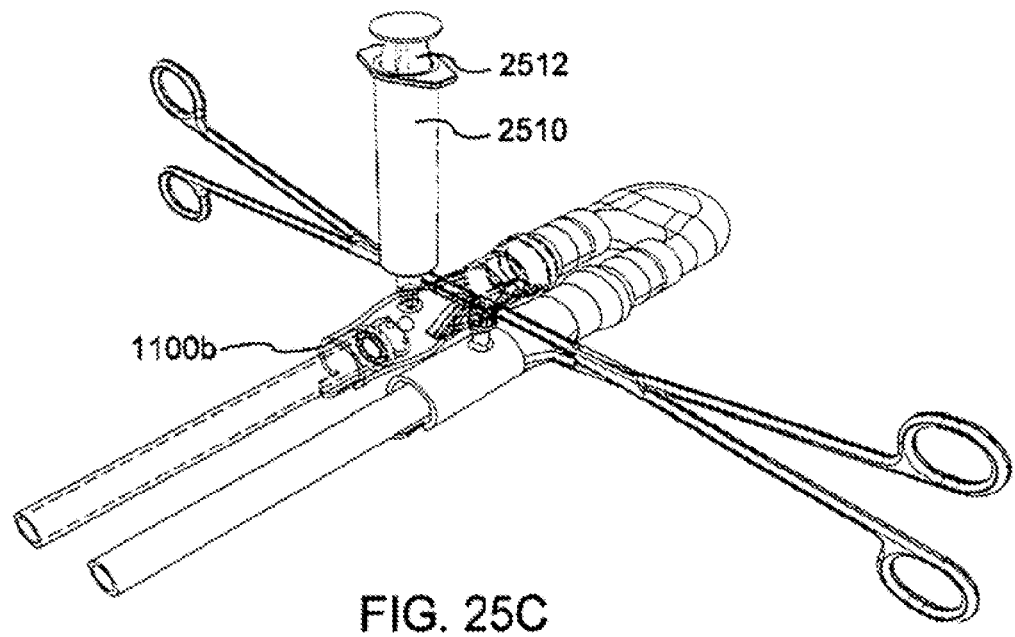

As the second cannula 1720 is inserted in the second DIP device 1100b, air bubbles 2502 may form in the space inside the second DIP device 1720 as shown in FIG. 25A. These air bubbles may be removed utilizing a syringe that is inserted into the external conduit 2504 of the second DIP device 1100*b* after removing the male plug 126 from female plug 120 (FIGS. 1, 2, and 3). In FIG. 25B, the syringe 2510, filled with a liquid and with plunger 2512 extended, is shown inserted into the external conduit 2504 of the second DIP device 1100*b*. In FIG. 25C, the plunger 2512 of the syringe 2510 is shown depressed downward, which injects the liquid into the second DIP device 1100*b*, thus creating additional pressure in the second DIP device 1100*b*.

Figure 25D:
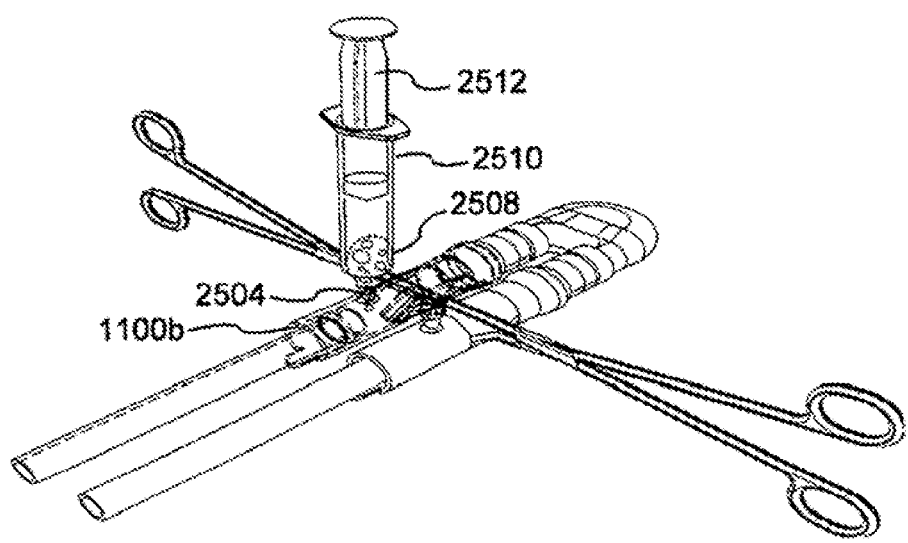
Figure 26:
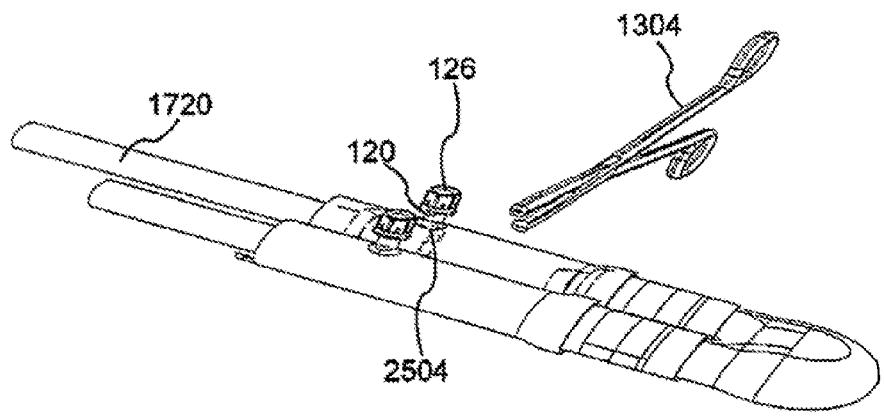
FIG. 26 illustrates removal of the clamp occluding the second DIP device during the insertion of the inflow cannulae to the VAD.
Figure 27:
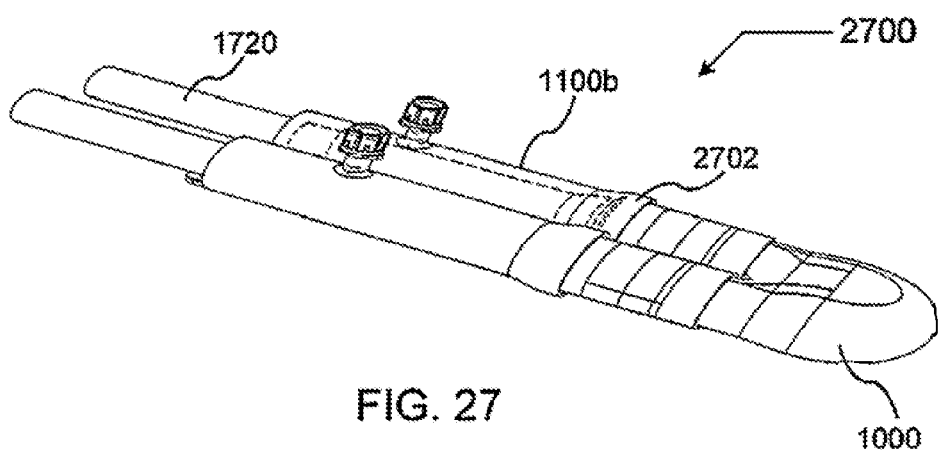
FIG. 27 illustrates the inflow cannulae connected to the outflow of the VAD.

Turning to FIG. 25D, the plunger 2510 is shown with the plunger 2512 extended upward. This causes the air bubbles 2508 to be extracted from the second DIP device 1100*b* into the syringe 2510. Once this is done, the syringe 2510 is removed from the external conduit 2504 of the second DIP device 1100*b*, the male plug 126 is fitted back over the female plug 120 (FIGS. 1, 2, and 3), and the clamp 1104 is removed, as shown in FIG. 26. FIG. 27 shows the cannula 1720 inserted further into the second DIP device 1100*b* until a connection is established at connector 2004 with the outflow port of the VAD 1000. The result is an air-purged, bubble-free VAD/DIP device/cannulae assembly 2700.

Figure 28A:
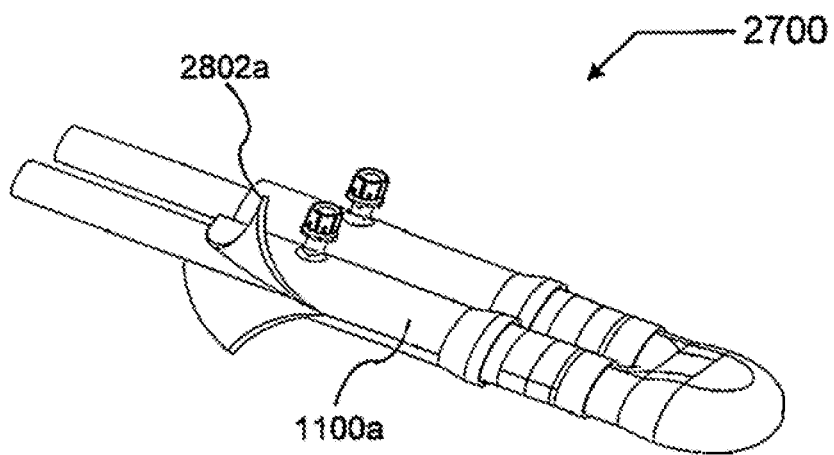
FIGS. 28A and 28B illustrate removal of one of the DIP devices from the connection between the cannulae and the VAD.
Figure 28B:
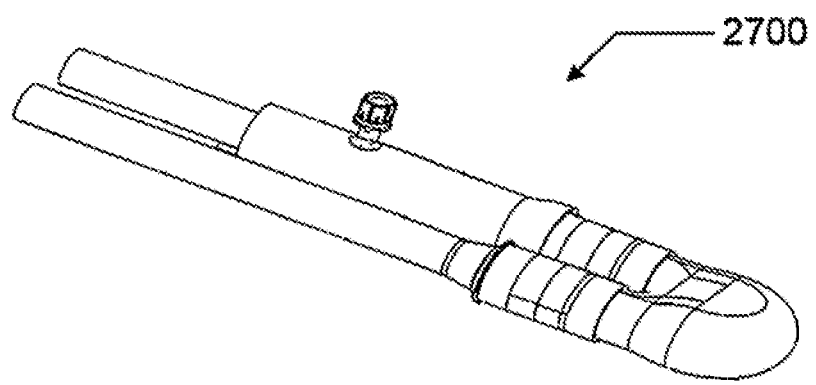
Figure 29A:
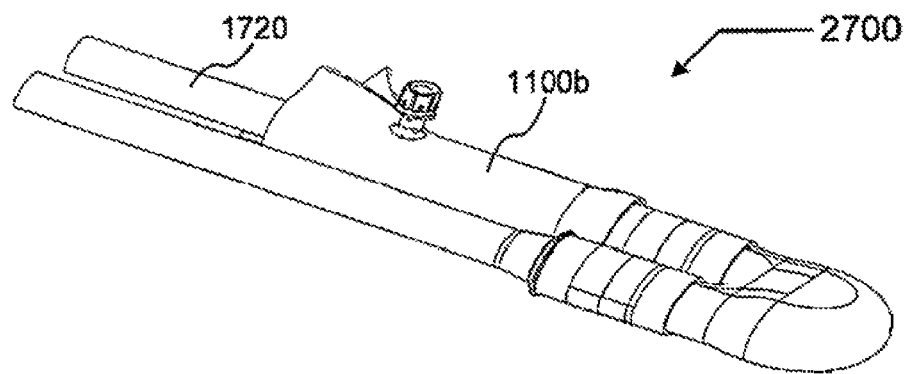
FIGS. 29A and 29B illustrate removal of the second DIP device.
Figure 29B:
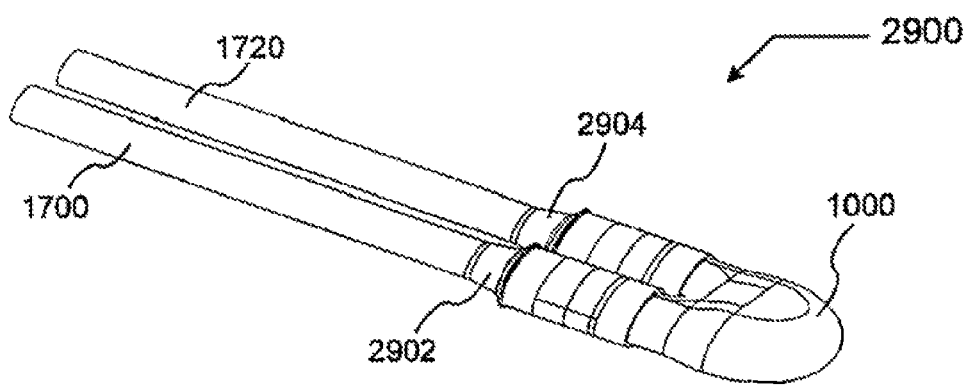

In general, FIGS. 28A and 28B illustrate removal of the first DIP device 1100*a* from the VAD/DIP device/cannulae assembly 2700 and FIGS. 29A and 29B illustrate removal of the second DIP device 1100*b*. The first DIP device 1100*a* is detached from the VAD/DIP device/cannulae assembly 2700 by pulling on the flap 2802*a*, leaving the assembly 2700 shown in FIG. 28B. This process is repeated for the second cannula 1720 as shown in FIG. 29A, with the end result being the cannulae/VAD assembly 2900 shown in FIG. 29B, where cannulae 1700 and 1720 are shown connected to VAD 1000 through connectors 2902 and 2904, respectively.

Figure 30:
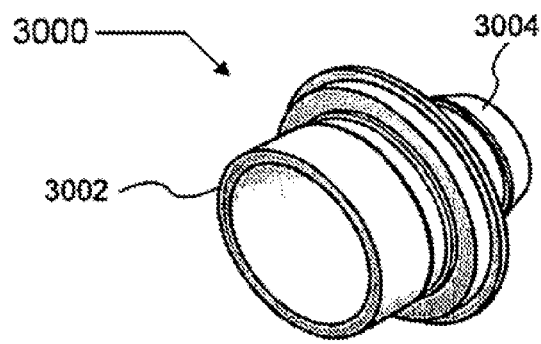
FIG. 30 shows an example connector that may be used to connect cannulae to a VAD ad shown in FIG. 29B.
Figure 31:
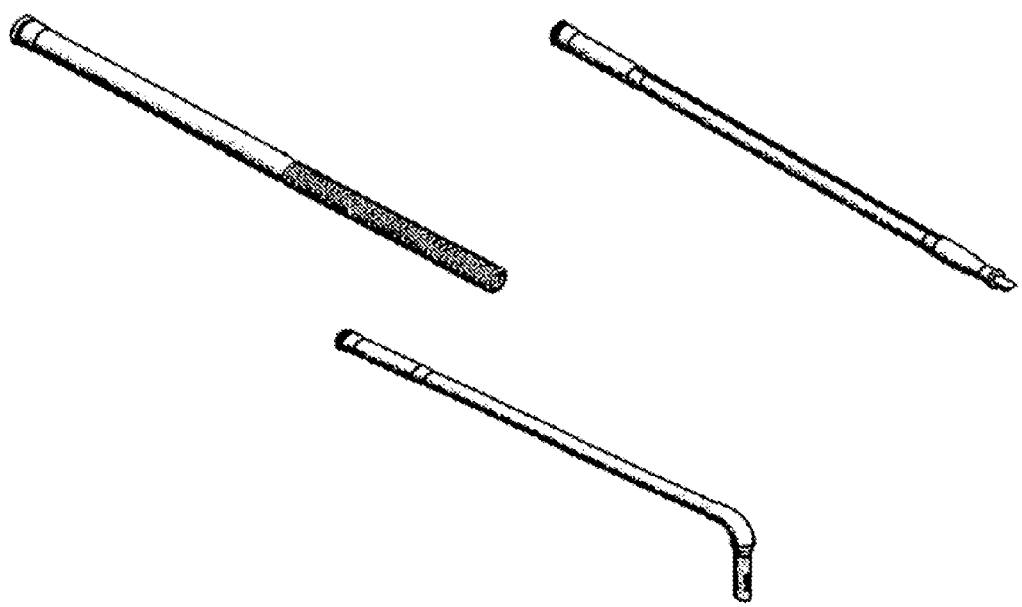
FIG. 31 shows three (3) examples of cannulae that may be utilized in accordance with the invention.

FIG. 30 shows an example connector 3000 that may be used to connect cannulae to a VAD, such as connectors 2902 and 2904 as shown in FIG. 29. Connector 3000 has a distal ending 3002 and a proximal ending 3004 and may be attached to the inflow and outflow ports (not shown) of a VAD, with the distal ending 3002 attached to the ports. The DIP devices are then attached at the proximal ending 3004 and later the distal endings of the cannulae are also attached. The connector 3000 may be adapted to the cannulae to be attached so as to reduce turbulence in the fluid flow throughout the cardiac circulatory support system and to avoid flow drain from the system or air inflow into the system. The connector 3000 may be made of stainless steel or other suitable material. FIG. 31 shows three (3) examples of cannulae that may be utilized in accordance with the invention, such as cannulae 1700 and 1720 shown in FIG. 29B.

Figure 32:
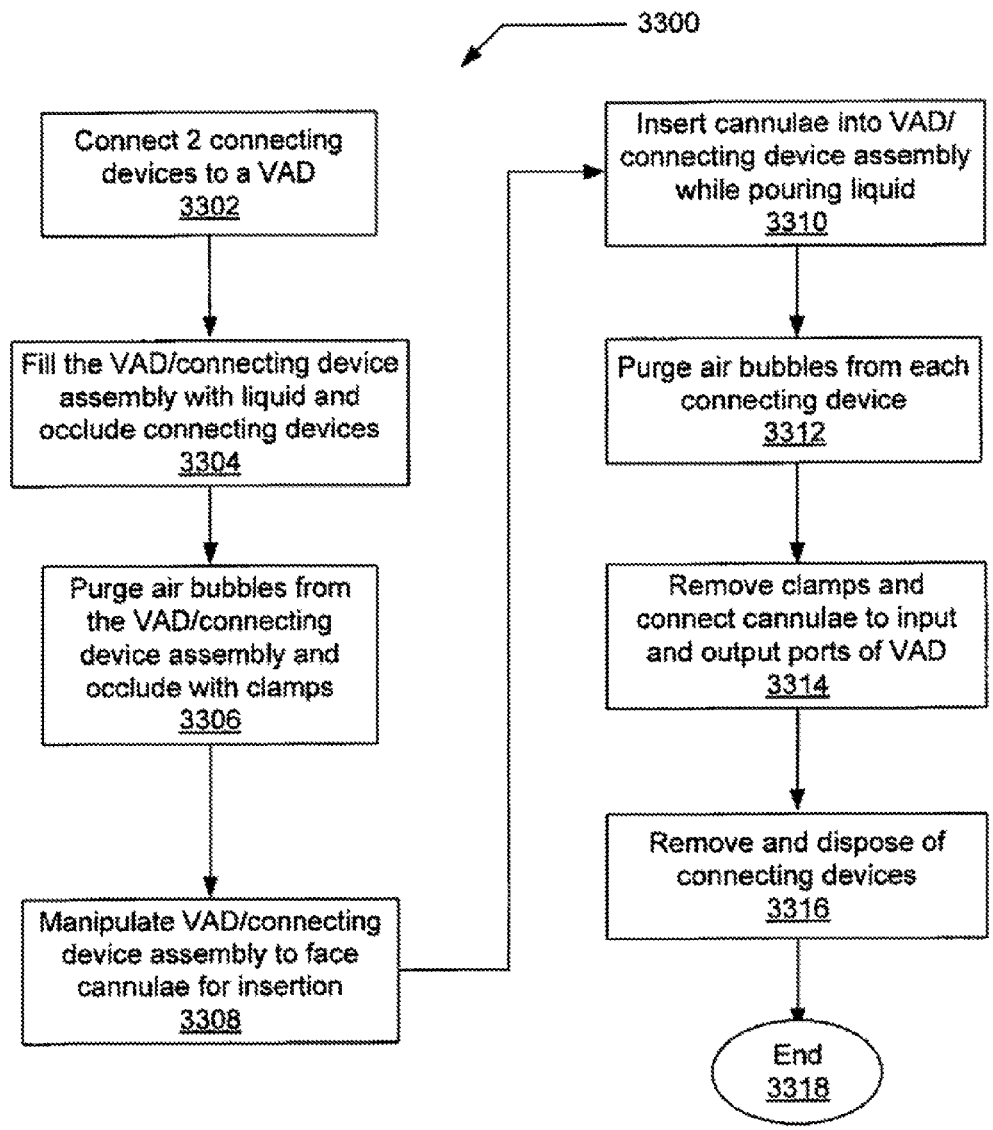
FIG. 32 shows a flowchart illustrating an example method of operation that uses a DIP device in accordance with the invention to connect cannulae to a cardiac circulatory support deviced and then purge any air bubbles that may have entered the cannulae/cardiac circulatory support device assembly using the DIP device.

FIG. 32 shows a flowchart illustrating an example method of operation that uses DIP services in accordance with the invention to connect cannulae to a cardiac circulatory support device and then, using the DIP device, to purge any air bubbles that may have entered the cannulae/cardiac circulatory support device assembly. The method of operation starts in step 3302 where a DIP device is connected to the inflow and outflow ports of a cardiac circulatory support device, which in this example method is a ventricular assist device ("VAD"). This connection is made utilizing connectors that are attached to the ports of the VAD and one DIP device is attached to the proximal ending of each connector.

In step 3304, the VAD/DIP assembly is turned VAD-side down, and a liquid is poured into both DIP devices. Each of the DIP devices may then be occluded with a clamp. Next, in step 3306, air bubbles are purged from the VAD/DIP assembly by inverting the VAD/DIP assembly, removing one of the clamps from a DIP device, and pouring more liquid into the DIP device to force the trapped air out the distal ending of the DIP device. This sequence of steps is illustrated in FIGS. 15A and 15B.

In step 3308, the occluded VAD/DIP assembly is maneuvered so as to position the distal endings of the cannulae facing the distal endings of the assembly, as shown in FIG. 17A. In next step 3310, the cannulae are inserted into the VAD/DIP assembly while pouring liquid into the distal endings of the cannulae and the DIP device, and also pouring the liquid over the gap between the cannulae and the DIP devices when inserting the cannulae into the DIP devices.

In step 3312, the air bubbles are purged from each of the DIP devices. More details of this process are shown in FIGS. 25A, 25B, 25C, and 25D. In step 3314, the clamps are removed from the DIP devices and the cannulae are moved further into the DIP devices until a connection is made between the cannulae and the connectors attached to the VAD.

In step 3316, the DIP devices are removed from the VAD/ DIP device/cannulae assembly, as shown in FIGS. 28A, 28B, 29A, and 29B. The process ends in step 3318, with the cannulae/VAD assembly that is shown in FIG. 29B.

While various implementations of the invention have been described, it will be apparent to those of ordinary skill in the art that many more embodiments and implementations are possible that are within the scope of this invention. Moreover, it will be understood that the foregoing description of an implementation has been presented for purposes of illustration and description or may be acquired from practicing the invention. The claims and their equivalents define the scope of the invention.

What is claimed is:

1. A method for connecting cannulae to a cardiac circulatory support device, the method comprising:
    connecting an inflow disposable purging ("DIP") device and an outflow DIP device to an inflow port and an output port, respectively, of a cardiac circulatory support device to form a support device/DIP device assembly;
    purging the support device/DIP device assembly of trapped air;
    occluding the inflow DIP device and the outflow DIP device;
    inserting an outflow cannula into the inflow DIP device and an inflow cannula into the outflow DIP device;
    purging air bubbles from each of the inflow DIP device and the outflow DIP device; and
    connecting the cannulae to the cardiac circulatory support device to form a support device/DIP device/cannulae assembly.

2. The method of claim 1, further including the step of removing the inflow DIP device and the outflow DIP device from the support device/DIP device/cannulae assembly.

3. The method of claim 1, wherein the step of connecting the inflow DIP device and the outflow DIP device to the cardiac circulatory support device includes attaching a connector to the inflow port and to the outflow port of the cardiac circulatory support device.

4. The method of claim 1, wherein the step of purging the support device/DIP device assembly of trapped air includes:
    filling the support device/DIP device assembly with a liquid;
    occluding one of the DIP devices;
    pouring additional liquid into the other DIP device to force the trapped air out of a distal ending of the other DIP device; and
    occluding the other DIP device.

5. The method of claim 4, where the liquid is a saline solution.

6. The method of claim 1, where the step of inserting an outflow cannula into the inflow DIP device and an inflow cannula into the outflow DIP device includes:
   positioning the support device/DIP device assembly facing distal endings of the outflow and inflow cannulae;
   inserting the outflow cannula into the inflow DIP device while pouring a liquid over the distal ending of the outflow cannulae and a distal ending of the inflow DIP device;
   removing the occlusion from the inflow DIP device; and
   further inserting the outflow cannula into the inflow DIP device until the outflow cannula connects to the inflow port of the cardiac circulatory support device.

7. The method of claim 6, further including the step of repeating the steps of claim 1 for the inflow cannula and the outflow DIP device.

8. The method of claim 7, where the step of purging air bubbles from each of the inflow DIP device and the outflow DIP device includes extracting the air bubbles from the DIP devices using a syringe inserted into an external conduit of the DIP devices.

9. The method of claim 7, where the liquid is a saline solution.

10. The method of claim 1, where the cardiac circulatory support device is a ventricular assist device ("VAD").

\* \* \* \* \*